US008709761B2

(12) United States Patent
Howard et al.

(10) Patent No.: US 8,709,761 B2
(45) Date of Patent: Apr. 29, 2014

(54) METHODS OF SACCHARIFICATION OF POLYSACCHARIDES IN PLANTS

(75) Inventors: John Howard, Cayucos, CA (US); Gina Fake, Arryo Grande, CA (US)

(73) Assignee: Applied Biotechnology Institute, Inc., San Luis Obispo, CA (US)

( * ) Notice: Subject to any disclaimer, the term of this patent is extended or adjusted under 35 U.S.C. 154(b) by 176 days.

(21) Appl. No.: 13/025,659

(22) Filed: Feb. 11, 2011

(65) Prior Publication Data

US 2011/0143398 A1    Jun. 16, 2011

Related U.S. Application Data

(63) Continuation-in-part of application No. 12/901,507, filed on Oct. 9, 2010.

(60) Provisional application No. 61/254,040, filed on Oct. 22, 2009.

(51) Int. Cl.
*C12P 19/00* (2006.01)

(52) U.S. Cl.
USPC .............................. 435/72; 435/277

(58) Field of Classification Search
None
See application file for complete search history.

(56) References Cited

U.S. PATENT DOCUMENTS

| 5,981,835 | A | 11/1999 | Austin-Phillips |
| 6,013,860 | A | 1/2000 | Himmel |
| 6,504,085 | B1 | 1/2003 | Howard |
| 6,818,803 | B1 | 11/2004 | Austin-Philis |
| 7,361,806 | B2 | 4/2008 | Lebel |
| 2003/0109011 | A1 | 6/2003 | Hood |
| 2006/0026715 | A1 | 2/2006 | Howard |
| 2008/0022425 | A1 | 1/2008 | Lebel et al. |
| 2008/0078005 | A1 | 3/2008 | Lebel |
| 2009/0205086 | A1 | 8/2009 | Howard |
| 2011/0097786 | A1 | 4/2011 | Howard |

FOREIGN PATENT DOCUMENTS

| WO | WO9839461 A1 | 9/1998 |
| WO | WO9916890 A2 | 4/1999 |
| WO | WO0004146 A1 | 1/2000 |

OTHER PUBLICATIONS

Han et al. (2008) "Characteriziation of beta-glucosidase from corn stover and its application in simultaneous saccharification and fermentation" Bioresource Technology 99:6081-6087, available online Feb. 20, 2008.
Han et al. (2007)"Synergism between corn stover protein and cellulase" Enzyme and Microbrial Technology 41:638-645.
Han et al. (2010) "Biochemical characterization of a maize stover beta-exoglucanase and its use in lignocellulose conversion" Bioresource Technology 101:6111-6117, available online Mar. 20, 2010.
Han et al. (2010) "Synergism between hydrophobic proteins of corn stover and cellulase in lignocellulose hydrolysis" Biochemical Engineering Journal 48:218-224.
Ingle et al. (1965) "Changes in composition during development and maturation of maize seeds" Plant Physiology 40 (5), 835-839.
"Typical Composition of Yellow Dent Corn" by Bunge North America, of Bunge Limited at: www.bungenorthamerica.com/news/pubs/03_Bunge_Milling_Process_Diagram.pdf (2011).
Kusnadi et al., 1997. Biotechnology and Bioengineering. 56:473-484.
Sticklen, 2006 Curr Opin Biotechnol 17:315-9.
Dai et al. (2000) Improved plant-based production of E1 endoglucanase using potato: expression optimization and tissue targeting. Molecular breeding 6:277-285.
Dai et al. (1999) Expression of *Trichoderma reesei* Exo cellobiohydrolast I in transgenic tobacco leaves and call, Applied Biochemistry and Biotechnology, vol. 77-79:689-699.
Dai et al. (1998) Over-expression of cellulase in transgenic tobacco whole plants, Poster: ASPP Annual Meeting, vol. 1998, p. 85.
Hood (2002) Industrial proteins produced from transgenic plants, in: E. Hood and J. Howard (Eds.), Plants as factories for protein production, Kluwer Academic Publishers, The Netherlands. pp. 119-135.
Hood E(2003) Production and application of proteins from transgenic plants, Kluwer Academic Publishers. pp. 377.
Howard et al. (2011) Enzyme production systems for biomass conversion. In E.E. Hood, P. Nelson, & R. Powell (Eds.), Plant biomass conversion (pp. 227-253). Singapore: John Wiley & Sons Inc.
Woodard et al. (2003) Maize (*Zea mays*)-derived bovine trypsin: characterization of the first large-scale, commercial protein product from transgenic plants. Biotechnology and applied biochemistry 38:123-130.
Zeigelhoffer et al (1999) Expression of bacterial cellulase genes in transgenic alfalfa (*Medicago sativa* L.), potato (*Solanum tuberosum* L.) and tobacco (*Nicotiana tabacum* L.). Molecular breeding : new strategies in plant improvement 5:309-318.
Ziegler et al. (2000) Accumulation of a thermostable endo-1, 4- -D-glucanase in the apoplast of *Arabidopsis thaliana* leaves. Molecular Breeding 6:37-46.
Horvath et al. (2000) "The production of recombinant proteins in transgenic barley grains" PNAS vol. 97, pp. 1914-1919.
Gusakov et al. (2007) Design of highly efficient cellulase mixtures for enzymatic hydrolysis of cellulose. Biotechnology and bioengineering 97:1028-1038.
Sticklen. (2008) Plant genetic engineering for biofuel production: towards affordable cellulosic ethanol. Nat Rev Genet 9:433-43.

(Continued)

*Primary Examiner* — Lisa J Hobbs
(74) *Attorney, Agent, or Firm* — Patricia A. Sweeney

(57) ABSTRACT

Saccharification of polysaccharides of plants is provided, where release of fermentable sugars from cellulose is obtained by adding plant tissue composition. Production of glucose is obtained without the need to add additional β-glucosidase. Adding plant tissue composition to a process using a cellulose degrading composition to degrade cellulose results in an increase in the production of fermentable sugars compared to a process in which plant tissue composition is not added. Using plant tissue composition in a process using a cellulose degrading enzyme composition to degrade cellulose results in decrease in the amount of cellulose degrading enzyme composition or exogenously applied cellulase required to produce fermentable sugars.

22 Claims, 24 Drawing Sheets

(56) References Cited

OTHER PUBLICATIONS

Cho et al. (2010) Expansins as agents in hormone action. In: Plant Hormones: Biosynthesis, Signal Transduction, Action! (ed. by Peter J Davies), Kluwer, Dordrecht, pp. 262-281.

Kawazu et al. (1996) "Expression of a *Ruminococcus albus* cellulase gene in tobacco suspension cells" Journal of Fermentation and Bioengineering vol. 82, No. 3, 205-209.

Kawazu et al. (1999) "Expression of a bacterial endoglucanase gene in tobacco increases digestibility of its cell wall fibers" Journal of Bioscience and Bioengineering vol. 88 No. 4, 421-425.

Jensen et al. (1998) "Inheritance of a codon-optimized transgene expressing heat stable (1,3-1,4)-beta-glucanase in scutellum and aleurone of germinating barely" Hereditas 129:215-225.

Oraby et al. (2007) Enhanced conversion of plant biomass into glucose using transgenic rice-produced endoglucanase for cellulosic ethanol. Transgenic Research 16:739-749.

Jimenez-Flores et al. (2010) "A novel method for evaluating the release of fermentable sugars from cellulosic biomass" Enzyme and Microbial Technology 47: 206-211.

Hayden et al. (2011) "Synergistic activity of plant extracts with microbial cellulases for the release of free sugars" BioEnergy Research 5.2: 398-406.

Sun et al. (2007) "Expression and characterization of Acidothermus cellulolyticus E1 endoglucanase in transgenic duckweed Lemna minor 8627" Bioresource Technology 98.15: 2866-2872.

Yu et al. (2007) "Expression of thermostable microbial cellulases in the chloroplasts of nicotine-free tobacco" Journal of Biotechnology 131.3: 362-369.

Time (in hours)

Figure 10 A and 10B
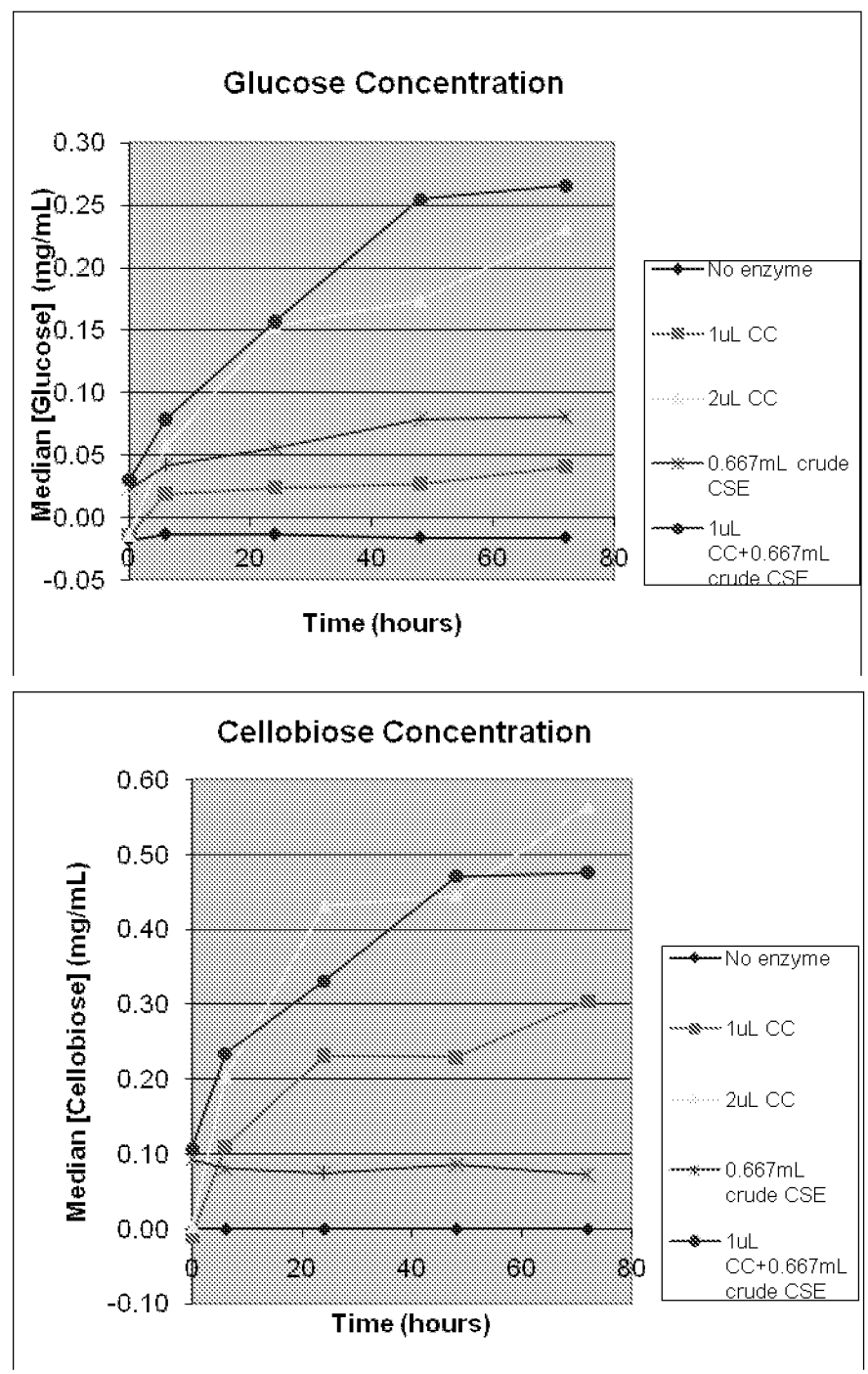

METHODS OF SACCHARIFICATION OF POLYSACCHARIDES IN PLANTS

REFERENCE TO RELATED APPLICATION

This application is a continuation-in-part of previously filed and co-pending application U.S. Ser. No. 12/901,507, filed Oct. 9, 2010, which claims priority to application U.S. Ser. No. 61/254,040, filed Oct. 22, 2009, the contents of each are incorporated herein in their entirety.

STATEMENT REGARDING FEDERALLY SPONSORED RESEARCH OR DEVELOPMENT

This work was made with Government support under contract DE FG36 08GO88025 awarded by the Department of Energy and under contract Award # N00014-07-1-1152 awarded by the Department of the Navy, Office of Naval Research. The Government has certain rights in the invention. This work was made with Government support under contract SBIR 2010-33610-20956 awarded by the United States Department of Agriculture.

FIELD OF THE INVENTION

The present invention relates to methods of saccharification of polysaccharides in plants, and methods which provide for increased production of fermentable sugars at reduced cost.

BACKGROUND OF THE INVENTION

Polysaccharide degrading enzymes are useful in a variety of applications, such as in animal feed, industrial applications, and, in particular, in ethanol production.

Fossilized hydrocarbon-based energy sources, such as coal, petroleum and natural gas, provide a limited, non-renewable resource pool. Because of the world's increasing population and increasing dependence on energy sources for electricity and heating, transportation fuels, and manufacturing processes, energy consumption is rising at an accelerating rate. The US transportation sector alone consumes over 100 billion gallons of gasoline per year. Most (~60%) of the oil used in the US today is imported, creating a somewhat precarious situation in today's political climate because supply disruptions are highly likely and would cripple the ability of the economy to function. Fossil petroleum resources, on which our standard of living currently depends, will likely be severely limited within the next 50-100 years.

The production of ethanol from cellulosic biomass can utilize large volumes of agricultural resources that are untapped today. Ethanol is key to partially replacing petroleum resources, which are limited. Ethanol fuels burn cleanly and because of this, ethanol replacement of petroleum fuels at any ratio will have a positive impact on the environment. Production of ethanol from domestic, renewable sources also ensures a continuing supply. For these reasons, the production of ethanol fuels from cellulosic biomass are being developed into a viable industry. High yields of glucose from cellulose (using cellulase enzymes) are required for any economically viable biomass utilization strategy to be realized. The US is one country involved in ethanol production and currently manufactures approximately over three billion gallons of ethanol from corn grain-derived starch. (American Coalition of Ethanol Production, www.ethanol.org; also, Sheehan, J. "The road to bioethanol: A strategic perspective of the US Department of Energy's National Ethanol Program" Himmel M E, Baker J O, Saddler J N eds., *Glycosyl Hydrolases for Biomass Conversion,* 2-25). Ethanol that is produced from corn starch, however, is limited as an alternative to fossil fuels.

Unharvested residues from agricultural crops are estimated at a mass approximately equal to the harvested portion of the crops. Specifically for the corn crop, if half of the residue could be used as a feedstock for the manufacture of ethanol, then about 120 million tons of corn stover would be available annually for biomass conversion processes (Walsh, Marie E. Biomass Feedstock Availability in the United States. State Level Analysis. 1999). Assuming that mature, dry corn stover is approximately 40% cellulose on a dry weight basis then 48 million tons of cellulose/year would be available for hydrolysis to glucose. Using today's technology, a ton of cellulose will yield approximately 100 gallons of ethanol.

Because known technologies for ethanol production from cellulosic biomass have been more costly than the market price for ethanol, cellulosic ethanol will not become an important alternative to fossil fuels, unless the price of fossil fuels rises substantially. If, however, the cost of the production of ethanol from plant biomass could be reduced, then ethanol might become a cost-effective alternative to fossil fuels even at today's prices for fossil fuels.

Plant biomass is a complex matrix of polymers comprising the polysaccharides cellulose and hemicellulose, and a polyphenolic complex, lignin, as the major structural components. Any strategy designed to substitute cellulosic feedstocks for petroleum in the manufacture of fuels and chemicals must include the ability to efficiently convert the polysaccharide components of plant cell walls to soluble, monomeric sugar streams. Cellulose, the most abundant biopolymer on earth, is a simple, linear polymer of glucose. However, its semi-crystalline structure is notoriously resistant to hydrolysis by both enzymatic and chemical means. Yet, high yields of glucose from cellulose are critical to any economically viable biomass utilization strategy.

Nature has developed effective cellulose hydrolytic machinery, mostly microbial in origin, for recycling carbon from plant biomass in the environment. Without it, the global carbon cycle would not function. To date, many cellulase genes have been cloned and sequenced from a wide variety of bacteria, fungi and plants, and many more certainly await discovery and characterization (Schulein, M, 2000. Protein engineering of cellulases. *Biochim. Biophys. Acta* 1543:239-252); Tomme P, et al. 1995. Cellulose Hydrolysis by Bacteria and Fungi. *Advances in Microbial Physiology* 37:1-81). Cellulases are a subset of the glycosyl hydrolase superfamily of enzymes that have been grouped into at least 13 families based on protein sequence similarity, enzyme reaction mechanism, and protein fold motif.

At present enzyme production is primarily by submerged culture fermentation. The scale-up of fermentation systems for the large volumes of enzyme required for biomass conversion would be difficult and extremely capital intensive. For purposes of comparison, a single very large (1 million liter), aerobic fermentation tank could produce 3,091 tons of cellulase protein/yr in continuous culture. Currently, however, fermentation technology is practiced commercially on a significantly smaller scale and in batch mode, so production capacities are closer to 10% of the theoretical 3,091 tons calculated above. Thus, using these assumptions, current practices would yield 3000 times less than the 1.2 MM tons of enzyme needed to convert the cellulose content from 120 MM tons per year of corn stover. Capital and operating costs of such a fermentative approach to producing cellulases are likely to be impractical due to the huge scale and capital investment that will be required.

A system which would reduce the costs associated with providing such enzymes and/or increase production of fermentable sugars produced in saccharification of plant polysaccharides would be highly beneficial.

SUMMARY OF THE INVENTION

Production of fermentable sugars in a saccharification process of plant polysaccharides is enhanced by providing plant tissue composition in the saccharification process. The plant tissue composition can be added to an exogenous source of a cellulose degrading enzyme, or can itself be transformed such that it expresses a heterologous cellulase protein and provides the exogenous enzyme. When a plant tissue composition is added to the process, production of fermentable sugars is increased compared to the processes which does not add plant tissue composition. In another embodiment, the amount of exogenously added cellulase enzymes or the composition comprising cellulase enzymes can be reduced while achieving release of fermentable sugars. Addition of plant tissue with a cellulose degrading enzyme composition produces glucose as a fermentable sugar, without the need to add β-D glucosidase. Tissue is maintained at a temperature such that endogenous enzymes are not degraded and may be used to enhance glucose production or as the source of both cellulase and glucose production.

DESCRIPTION OF THE DRAWINGS

FIG. 10 is a graph showing the amount of glucose (FIG. 10A) or cellobiose concentration (FIG. 10B) when cellulose was incubated with no enzymes, varying concentrations of commercial enzyme mixtures, seed extract (CSE) and see extract combined with a microbial cellulase mixture as measure by HPLC.

DETAILED DESCRIPTION OF THE PREFERRED EMBODIMENTS

Figure 1:
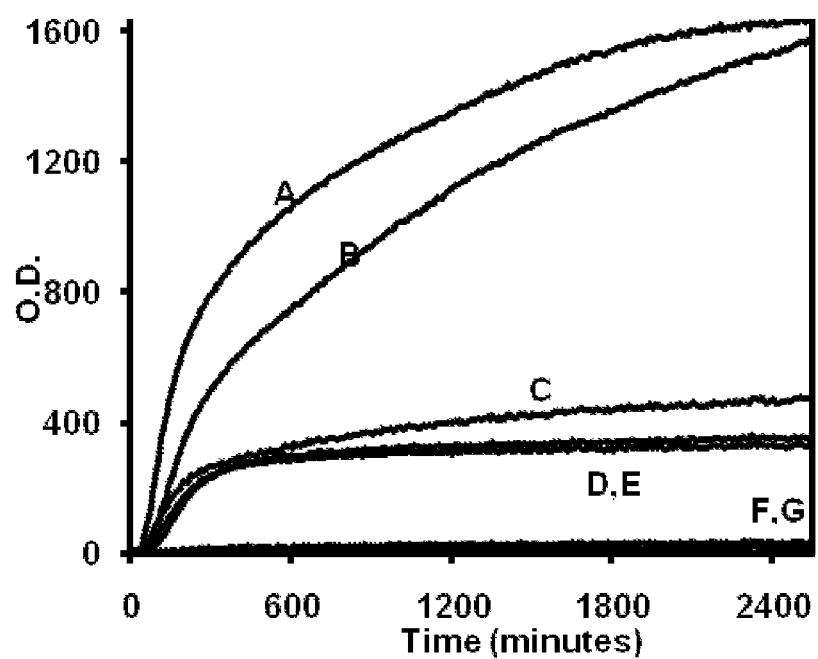
FIG. 1 is a graph showing yeast growth by measuring the change in optical density (OD) over time. Treatments include: samples made either with: A) cellulose+yeast+glucose; B) cellulose+yeast+enzymes; C) yeast+enzymes; D) yeast+cellulose; E) yeast; F) cellulose+enzymes; G) enzymes.

All references cited herein are incorporated herein by reference. Examples are provided to illustrate embodiments of the invention but are not intended to limit the scope of the invention.

The present invention is drawn to cost-effective methods for saccharification of polysaccharides, by adding a plant tissue composition and thereby increasing the amount of fermentable sugars produced in such a process using the same or lower amounts of cellulose degrading enzyme composition or reducing the amount of exogenous enzymes to achieve saccharification. The cellulose degrading enzymes are among the most prohibitive costs of this process, and avoiding the need to use one or more such enzymes is of considerable benefit. Increasing fermentable sugar production from cellulase or lowering the cost of exogenously applied enzymes is also highly desirable.

The methods of the invention involve the use of cellulosic biomass that is currently underutilized for the production of energy. By "cellulosic biomass" or feedstock is intended biomass that is comprised of plant cell walls and the components therein including, but not limited to, cellulose, hemicellulose, pectin, and lignin. Such cellulosic biomass includes, for example, crop plant residues or undesired plant material that may be left behind in the field after harvest or separated from the desired plant material or forest products or the like. A crop refers to a collection of plants grown in a particular cycle. By "desired plant material" is intended the plant product that is the primary reason for commercially growing the plant. Such desired plant material can be any plant or plant part or plant product that has commercial value. Corn is grown for human and animal consumption, as well as to produce products such as industrial oils, fertilizer and many other uses. Soybeans and wheat are used primarily in food products. There are multitudes of purposes for which these plant materials can be utilized. The desired plant material also includes protein produced by a transgenic polynucleotide. In short, the desired plant material refers to any product from the plant that is useful. The invention allows for profitable use of desired plant material or what would otherwise be low value or waste material after the desired plant is harvested. What is more, one skilled in the art understands that the production of the plant material for use as plant tissue composition in the process of the invention may in itself be production of desired plant material such as when crops such as switch grass are grown for the purpose of producing an energy source. In an embodiment of the invention, an enzyme substitute and/or an enzyme expressed as a heterologous protein in the plant can be used to degrade polysaccharides in a crop and can be produced by the very crop that will be degraded, thereby providing clear advantages in eliminating or reducing the need for an outside source of the enzyme, compacting costs with its production by combining it with production of the cellulose source. In addition, one skilled in the art can appreciate that the transgenic enzymes expressed in such plants may be used in any commercial polysaccharide-degrading process, such as in providing additives to animal feed (See, for example Rode et al., "Fibrolytic enzyme supplements for dairy cows in early lactation" *J. Dairy Sci.* 1999 October; 82(1):2121-6); industrial applications, (for example, in detergent applications, see Winetzky, U.S. Pat. No. 6,565,6131; in biofinishing of denims, see Vollmond, WO 97/25468); treatment of genes, or, in a preferred embodiment, in the production of ethanol.

It is anticipated the invention can be used with monocotyledonous or dicotyledonous plants. Examples of monocotyledonous plants are plants which belong to the genus of *avena* (oat), *triticum* (wheat), *secale* (rye), *hordeum* (barley), *oryza* (rice), *panicum, pennisetum, setaria*, sorghum (millet), *zea* (maize). Dicotyledonous useful plants are, inter alia, leguminous plants, such as legumes and especially alfalfa, soybean, rape, tomato, sugar beet, and potato.

By a "crop plant" is intended any plant that is cultivated for the purpose of producing plant material that is sought after by man for either oral consumption, or for utilization in an industrial, pharmaceutical, or commercial process. The invention may be applied to any of a variety of plants, including, but not limited to maize, wheat, rice, barley, soybean, cotton, sorghum, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassaya, potato, carrot, radish, pea, lentils, cabbage, cauliflower, broccoli, Brussels sprouts, peppers, and pineapple, conifers and other trees, tree fruits such as citrus, apples, pears, peaches, apricots, walnuts, avocado, banana, and coconut; and flowers such as orchids, carnations and roses.

While such cellulosic biomass contains vast amounts of polysaccharides, these polysaccharides are not readily fermentable into ethanol. These polysaccharides are constituents of plant cell walls and include, but are not limited to, cellulose, hemicellulose, and pectin. The present invention provides cost-effective methods that involve converting at least a portion of these polysaccharides, particularly the portion comprising cellulose, into a form that can be readily fermented into ethanol by the microorganisms that are presently used for ethanol production, namely yeasts and bacteria. The invention can in an embodiment integrate the economical production of the enzyme substitute or enzymes required for the conversion of the polysaccharides in cellulosic biomass to ethanol with the production of the desired plant material and the simultaneous recovery of the desired material, the cellulosic raw material and the polysaccharide-degrading enzyme substitute or enzymes in a single harvest operation.

The methods of the invention involve the conversion of plant cell wall polysaccharides to fermentable sugars that can then be used in the production of ethanol or other desired molecules via fermentation methods known in the art. The use of the term "fermentable sugars" includes, but is not limited to, monosaccharides and disaccharides and also encompasses sugar derivatives such as, for example, sugar alcohols, sugar acids, amino sugars, and the like. The fermentable sugars of the invention encompass any sugar or sugar derivative that is capable of being fermented using microorganisms.

The enzymes used in saccharification processes currently encompass enzymes that can be employed to degrade plant cell wall polysaccharides into fermentable sugars. Such enzymes are known in the art and include, but are not limited to, enzymes that can catalyze the degradation of cellulose, hemicellulose, and/or pectin. In particular, the methods of the invention are drawn to cellulose-degrading enzymes. By "cellulose-degrading enzyme" is intended any enzyme that can be utilized to promote the degradation of cellulose into fermentable sugars including, but not limited to, cellulases and glucosidases. By way of example, without limitation, the enzymes classified in Enzyme Classification as 3.2.1.x are included within the scope of the invention. An example of the many enzymes which may be employed in the invention is presented in Table 1, a list of enzymes in the category by the Nomenclature Committee of the International Union of Biochemistry and Molecular Biology (NC-IUBMB).

TABLE 1

| Polysaccharide degrading enzymes | |
|---|---|
| EC 3.2.1.1 | α-amylase |
| EC 3.2.1.2 | β-amylase |
| EC 3.2.1.3 | glucan 1,4-α-glucosidase |
| EC 3.2.1.4 | cellulase |
| EC 3.2.1.6 | endo-1,3(4)-β-glucanase |
| EC 3.2.1.7 | inulinase |
| EC 3.2.1.8 | endo-1,4-β-xylanase |
| EC 3.2.1.10 | oligo-1,6-glucosidase |
| EC 3.2.1.11 | dextranase |
| EC 3.2.1.14 | chitinase |
| EC 3.2.1.15 | polygalacturonase |
| EC 3.2.1.17 | lysozyme |
| EC 3.2.1.18 | exo-α-sialidase |
| EC 3.2.1.20 | α-glucosidase |
| EC 3.2.1.21 | β-glucosidase |
| EC 3.2.1.22 | α-galactosidase |
| EC 3.2.1.23 | β-galactosidase |
| EC 3.2.1.24 | α-mannosidase |
| EC 3.2.1.25 | β-mannosidase |
| EC 3.2.1.26 | β-fructofuranosidase |
| EC 3.2.1.28 | αα-trehalase |
| EC 3.2.1.31 | β-glucuronidase |
| EC 3.2.1.32 | xylan endo-1,3-β-xylosidase |
| EC 3.2.1.33 | amylo-1,6-glucosidase |
| EC 3.2.1.35 | hyaluronoglucosaminidase |
| EC 3.2.1.36 | hyaluronoglucuronidase |
| EC 3.2.1.37 | xylan 1,4-β-xylosidase |
| EC 3.2.1.38 | β-D-fucosidase |
| EC 3.2.1.39 | glucan endo-1,3-β-D-glucosidase |
| EC 3.2.1.40 | α-L-rhamnosidase |
| EC 3.2.1.41 | pullulanase |
| EC 3.2.1.42 | GDP-glucosidase |
| EC 3.2.1.43 | β-L-rhamnosidase |
| EC 3.2.1.44 | fucoidanase |
| EC 3.2.1.45 | glucosylceramidase |
| EC 3.2.1.46 | galactosylceramidase |
| EC 3.2.1.47 | galactosylgalactosylglucosylceramidase |
| EC 3.2.1.48 | sucrose α-glucosidase |
| EC 3.2.1.49 | α-N-acetylgalactosaminidase |
| EC 3.2.1.50 | α-N-acetylglucosaminidase |
| EC 3.2.1.51 | α-L-fucosidase |
| EC 3.2.1.52 | β-L-N-acetylhexosaminidase |
| EC 3.2.1.53 | β-N-acetylgalactosaminidase |
| EC 3.2.1.54 | cyclomaltodextrinase |
| EC 3.2.1.55 | α-N-arabinofuranosidase |
| EC 3.2.1.56 | glucuronosyl-disulfoglucosamine glucuronidase |
| EC 3.2.1.57 | isopullulanase |
| EC 3.2.1.58 | glucan 1,3-β-glucosidase |
| EC 3.2.1.59 | glucan endo-1,3-α-glucosidase |
| EC 3.2.1.60 | glucan 1,4-α-maltotetraohydrolase |
| EC 3.2.1.61 | mycodextranase |
| EC 3.2.1.62 | glycosylceramidase |
| EC 3.2.1.63 | 1,2-α-L-fucosidase |
| EC 3.2.1.64 | 2,6-β-fructan 6-levanbiohydrolase |
| EC 3.2.1.65 | levanase |
| EC 3.2.1.66 | quercitrinase |
| EC 3.2.1.67 | galacturan 1,4-α-galacturonidase |
| EC 3.2.1.68 | isoamylase |
| EC 3.2.1.70 | glucan 1,6-α-glucosidase |

TABLE 1-continued

| Polysaccharide degrading enzymes | |
|---|---|
| EC 3.2.1.71 | glucan endo-1,2-β-glucosidase |
| EC 3.2.1.72 | xylan 1,3-β-xylosidase |
| EC 3.2.1.73 | licheninase |
| EC 3.2.1.74 | glucan 1,4-β-glucosidase |
| EC 3.2.1.75 | glucan endo-1,6-β-glucosidase |
| EC 3.2.1.76 | L-iduronidase |
| EC 3.2.1.77 | mannan 1,2-(1,3)-α-mannosidase |
| EC 3.2.1.78 | mannan endo-1,4-β-mannosidase |
| EC 3.2.1.80 | fructan β-fructosidase |
| EC 3.2.1.81 | agarase |
| EC 3.2.1.82 | exo-poly-α-galacturonosidase |
| EC 3.2.1.83 | κ-carrageenase |
| EC 3.2.1.84 | glucan 1,3-β-glucosidase |
| EC 3.2.1.85 | 6-phospho-β-galactosidase |
| EC 3.2.1.86 | 6-phospho-β-glucosidase |
| EC 3.2.1.87 | capsular-polysaccharide endo-1,3-α-galactosidase |
| EC 3.2.1.88 | β-L-arabinosidase |
| EC 3.2.1.89 | arabinogalactan endo-1,4-β-galactosidase |
| EC 3.2.1.91 | cellulose 1,4-β-cellobiosidase |
| EC 3.2.1.92 | peptidoglycan β-N-acetylmuramidase |
| EC 3.2.1.93 | αα-phosphotrehalase |
| EC 3.2.1.94 | glucan 1,6-α-isomaltosidase |
| EC 3.2.1.95 | dextran 1,6-α-isomaltotriosidase |
| EC 3.2.1.96 | mannosyl-glycoprotein endo-β-N-acetylglucosaminidase |
| EC 3.2.1.97 | glycopeptide α-N-acetylgalactosaminidase |
| EC 3.2.1.98 | glucan 1,4-α-maltohexaosidase |
| EC 3.2.1.99 | arabinan endo-1,5-α-L-arabinosidase |
| EC 3.2.1.100 | mannan 1,4-mannobiosidase |
| EC 3.2.1.101 | mannan endo-1,6-α-mannosidase |
| EC 3.2.1.102 | blood-group-substance endo-1,4-β-galactosidase |
| EC 3.2.1.103 | keratan-sulfate endo-1,4-β-galactosidase |
| EC 3.2.1.104 | steryl-β-glucosidase |
| EC 3.2.1.105 | strictosidine β-glucosidase |
| EC 3.2.1.106 | mannosyl-oligosaccharide glucosidase |
| EC 3.2.1.107 | protein-glucosylgalactosylhydroxylysine glucosidase |
| EC 3.2.1.108 | lactase |
| EC 3.2.1.109 | endogalactosaminidase |
| EC 3.2.1.110 | mucinaminylserine mucinaminidase |
| EC 3.2.1.111 | 1,3-α-L-fucosidase |
| EC 3.2.1.112 | 2-deoxyglucosidase |
| EC 3.2.1.113 | mannosyl-oligosaccharide 1,2-α-mannosidase |
| EC 3.2.1.114 | mannosyl-oligosaccharide 1,3-1,6-α-mannosidase |
| EC 3.2.1.115 | branched-dextran exo-1,2-α-glucosidase |
| EC 3.2.1.116 | glucan 1,4-α-maltotriohydrolase |
| EC 3.2.1.117 | amygdalin β-glucosidase |
| EC 3.2.1.118 | prunasin β-glucosidase |
| EC 3.2.1.119 | vicianin β-glucosidase |
| EC 3.2.1.120 | oligoxyloglucan β-glycosidase |
| EC 3.2.1.121 | polymannuronate hydrolase |
| EC 3.2.1.122 | maltose-6'-phosphate glucosidase |
| EC 3.2.1.123 | endoglycosylceramidase |
| EC 3.2.1.124 | 3-deoxy-2-octulosonidase |
| EC 3.2.1.125 | raucaffricine β-glucosidase |
| EC 3.2.1.126 | coniferin β-glucosidase |
| EC 3.2.1.127 | 1,6-α-L-fucosidase |
| EC 3.2.1.128 | glycyrrhizinate β-glucuronidase |
| EC 3.2.1.129 | endo-α-sialidase |
| EC 3.2.1.130 | glycoprotein endo-α-1,2-mannosidase |
| EC 3.2.1.131 | xylan α-1,2-glucuronosidase |
| EC 3.2.1.132 | chitosanase |
| EC 3.2.1.133 | glucan 1,4-α-maltohydrolase |
| EC 3.2.1.134 | difructose-anhydride synthase |
| EC 3.2.1.135 | neopullulanase |
| EC 3.2.1.136 | glucuronoarabinoxylan endo-1,4-β-xylanase |
| EC 3.2.1.137 | mannan exo-1,2-1,6-β-mannosidase |
| EC 3.2.1.139 | α-glucuronidase |
| EC 3.2.1.140 | lacto-N-biosidase |
| EC 3.2.1.141 | 4-α-D-{(1→4)-α-D-glucano}trehalose trehalohydrolase |
| EC 3.2.1.142 | limit dextrinase |
| EC 3.2.1.143 | poly(ADP-ribose) glycohydrolase |
| EC 3.2.1.144 | 3-deoxyoctulosonase |
| EC 3.2.1.145 | galactan 1,3-β-galactosidase |
| EC 3.2.1.146 | β-galactofuranosidase |
| EC 3.2.1.147 | thioglucosidase |
| EC 3.2.1.149 | β-primeverosidase |
| EC 3.2.1.150 | oligoxyloglucan reducing-end-specific cellobiohydrolase |
| EC 3.2.1.151 | xyloglucan-specific endo-β-1,4-glucanase |
| EC 3.2.1.152 | mannosylglycoprotein endo-β-mannosidase |

TABLE 1-continued

Polysaccharide degrading enzymes

| EC 3.2.1.153 | fructan β-(2,1)-fructosidase |
| EC 3.2.1.154 | fructan β-(2,6)-fructosidase |
| EC 3.2.1.156 | oligosaccharide reducing-end xylanase |

For the degradation of cellulose, two types of exoglucanase have been described that differ in their approach to the cellulose chain. One type attacks the non-reducing end and the other attacks the reducing end. Cellulase enzymes which cleave the cellulose chain internally are referred to as endo-β-1,4-glucanases (E.C. 3.2.1.4) and serve to provide new reducing and non-reducing chain termini on which exo-β-1,4-glucanases (cellobiohydrolase, CBH; E.C. 3.2.1.91) can operate (Tomme et al. (1995) *Microbial Physiology* 37:1-81). The product of the exoglucanase reaction is typically cellobiose, so a third activity, βD-glucosidase (E.C. 3.2.1.21), is required to cleave cellobiose to glucose. The exoglucanase can also yield longer glucose chains (up to 6 glucose units) that will require a β-D-glucosidase activity to reduce their size. Relative to the other enzyme activities needed for degradation of cellulose into fermentable sugars, only a minor amount of the β-D-glucosidase activity is required. In brief, current processes to produce fermentable sugars involve the addition to a cellulose-containing composition an endocellulase (endo-β-1,4-glucanases) and an exocellulase (exo-β-1,4-glucanases) which cleaves the cellulose chain internally. In order to produce the end product of glucose, a third enzyme is involved, a glucosidase (β-D-glucosidases), which acts on the cellobiose to produce glucose. One skilled understands that other proteins can increase the rate as, for example, expansins, which unfold the crystalline cellulose to make it more available so the enzymes can degrade it more efficiently. Cosgrove (1999) *Annu Rev Plant Physiol Plant Mol Biol* 50:391-417.

One reason that cellulose utilization has not yet been commercially realized is due to the high cost of the large quantities of cellulase enzymes required for its complete hydrolysis. Approximately 1.3 million tons/yr of cellulase may be required to convert the 48 million tons of stover-derived cellulose to glucose.

The inventors have surprisingly discovered that when plant tissue composition is added to a cellulase combination of endocellulase, and/or exocellulase and which may optionally include β-D glucosidase, increased fermentable sugar production occurs when compared to the same process without such tissue composition added. While the inventors found that unpurified plant-sourced proteins in other instances have not resulted in an active protein here, the inventors have produced unpurified plant tissue composition with enhance cellulose degradation properties despite the presence of potential inhibitors in plant tissue.

This can lead to a reduced amount of exogenously produced enzymes required thereby reducing the overall cost of bioconversion. What is more, the inventors have found that fermentable free sugars are produced from cellulose at rates of at 25% higher, 50% higher or any increment of over 25% with a set amount of exogenously applied enzymes. The sugars are produced at levels of at least two times as much, at least three times more, at least four times, at least five times as much and more when plant tissue composition is added to a cellulase combination of endocellulases, and/or exocellulases and/or β-D glucosidases, compared to fermentable sugars produced when no plant tissue composition is added to the combined cellulase composition. In addition, free sugars can be released with only the addition of at least one endocellulase and/or exocellulase and without adding exogenous β-D glucosidase. Through enzymatic biochemical assays, it has been determined there are cellulases present in plants, yet these amounts based on biochemical analysis are very low and one would not expect a complete process where fermentable free sugars are produced.

Yet, the surprising and unexpected result is that the process can produce fermentable sugars when adding plant tissue composition to at least one cellulase. The addition of plant tissue composition produced fermentable sugars when only one cellulase was added, without addition of other cellulose degrading enzymes. Without wishing to be bound by any theory, the inventors believe that a substance(s) in the plant substitutes for the enzymatic activity. Of particular significance is that when plant tissue composition is added, no β-D glucosidase is required to produce glucose. The plant tissue composition is believed to have provided a substance(s) which provides conversion of cellobiose to glucose. As a result, a process has been developed in which costs of producing fermentable free sugars is reduced by removing the need to add these expensive enzymes, and instead uses plant tissue composition as a substitute.

The invention also provides that one may reduce the protein load required to produce the fermentable sugars. The composition which is used for degrading the cellulose, including cellulases, and which may include enhancing proteins and the like, is in its entirety called the "protein load" in the industry. The protein load thus refers to the composition and components of the exogenous cellulose degrading enzyme composition, that is, the enzymes and proteins other than those found in native plant tissue. By referring to an exogenous cellulose degrading enzyme composition or exogenous cellulase composition is meant a cellulose degrading enzyme other than any endogenous enzyme present in the native plant tissue composition and includes such enzymes produced by a plant cell expressing a heterologous nucleic acid sequence encoding a cellulose degrading enzyme. As noted, the exogenous enzyme can be from any source outside those cellulose degrading enzymes which may be naturally found in the plant or at elevated levels of those that occur naturally in the plant. For example, commercially available cellulose degrading enzymes are widely available, as discussed herein. Further, a plant can be transformed with a nucleic acid molecule which then expresses a heterologous cellulose degrading enzyme protein in the plant. An example of production of endocellulases and exocellulases in plants is described at US Patent Publication No. 20060026715, incorporated herein by reference in its entirety, and also described in the examples below. In an embodiment, the plant cell-produced heterologous protein can serve as the source of exogenous cellulose degrading enzyme. It can be purified if desired, or the plant cells or tissue comprising the heterologous enzyme added to the mixture. In one embodiment, the plant tissue composition of the invention transformed with one or more cellulose degrading enzymes can be the source of enhancement of the production of fermentable sugars by providing plant tissue composition for such enhancement, and also provide one or more exogenous cellulose degrading enzymes. As shown infra, production of fermentable sugars from cellulose is enhanced when plant tissue composition is added to the saccharification process in which one or more exogenous cellulose degrading enzymes are used.

With the invention, the protein load can be reduced by eliminating an enzyme, reducing the amount of enzymes, or reducing the amount of the entire exogenous cellulose degrading enzyme composition and producing fermentable sugars. Presence of plant tissue composition allows for the reduction in enzymes and protein load and thereby provides the advantage of decreasing costs while yet producing fermentable sugars.

One may reduce the protein load in one embodiment by reducing the amount of the exogenous cellulase composition that needs to be added. Such a composition can be any composition of at least one cellulase and in another embodiment it can be combined with other cellulases (for example, endocellulases, exocellulase, β-D glucosidase, etc.) or enhancing proteins such as expansins. In one embodiment, exogenous cellulose degrading composition is reduced by at least 25%, in another embodiment by at least 50%, or reduced by any increment over 25%, and yet produce a cost effective amount of fermentable free sugars. In still another embodiment, the amount of enzyme in the exogenous cellulase composition can be reduced. In one embodiment, the enzyme is reduced by at least 25% in, in another embodiment by at least 50%, or reduced by any increment over 25%, and yet produce a cost effective amount of fermentable free sugars. In referring to a cost effective amount of fermentable free sugars, is meant that one is able to produce fermentable sugars in an amount that is the same as that produced when the protein load is not reduced, or at an amount which is reduced by a percentage more than predicted percentage of reduction when the amounts of cellulose and protein load are stoichiometrically equal. In other words, prior to the present invention, manufacturers of commercial enzyme combinations dictate what amounts are to be used of the combination to produce fermentable sugars. One then can measure the amount of fermentable sugars so produced, and, if desired, adjust upward by adding more enzymes to produce even more sugars. From this standard, one then can also readily predict how much reduction in fermentable sugars will result if the enzyme combination is reduced. With the present invention, the enzyme combination can be reduced, and the amount of predictable sugars exceeds the predicted reduction. Without intending to be limiting, for example, if the protein load and cellulose are provided at stoichiometrically equal amounts as a standard, a predicted amount of fermentable sugars is produced. Current expectations are that if the amount of protein load is reduced by 25%, fermentable sugars are produced at 75% of that predicted amount. With the present invention, the amount of fermentable sugars produced in comparison to this standard is in excess of that amount. In another example, if the protein load and cellulose are stoichiometrically equal a predicted amount of fermentable sugars is produced. If the protein load is reduced by 50%, fermentable sugars are produced at an amount of 50% of that predicted amount. Here, the fermentable sugars are produced at excess of that amount. By way of further example, without intending to be limiting, the commercially available enzyme combination Spezyme®, as discussed herein, contains an endocellulase, exocellulase and β-glucosidase. Specifications that accompany the sale of the product indicate that one uses 0.4 to 0.5 liters/metric ton of dry substance as a low point to begin optimization of enzyme dosage. For a pre-treated substrate, where a thermochemical step is employed to remove lignin and hemicellulase, the cellulose to glucose conversion will be about 80-90%. One then determines how much fermentable sugar is produced and increases the amount of Spezyme® if necessary. Where such adjustment results in one using 1.2 or more liters/metric ton of dry substance, for example, it is possible with process of the invention to reduce that amount by at least about 25%, to 0.3 liters/metric ton; and when reduced by 50% reduce the amount to 0.6 liters/metric ton, and achieve the same amount of release of fermentable sugars. Thus considerable cost savings are achieved by reducing the amount of protein load. The plant tissue can be the cellulose being degraded, which provides the endogenous enhancer and allows for reduction of protein load. In another embodiment plant tissue composition is added to the cellulose and enzyme mixture. Thus the amount of exogenous cellulase composition is reduced. The protein load may also be reduced by eliminating an enzyme, such as by eliminating a β-D glucosidase.

There are a number of advantages to a process which uses plant tissue as a source for reducing exogenous enzymes, or where increased fermentable sugars are produced when added to a combination of endocellulase, exocellulase and β-D glucosidase. First, if such a composition can be obtained from a relatively small amount of plant tissue at relatively low cost, it can be used directly to complement microbial preparations. One ideal location for this activity from a practical perspective would be the corn embryo (germ). The endosperm fraction is used for feed and fuel while the germ fraction is a by-product and can be easily obtained without interfering with the major uses of the grain. Second, the plant enzymes may give insight as to specific activities that are beneficial for specific substrates and can lead to designing new enzyme combinations that would be more effective.

This general strategy can be used for plants and maize in particular and is an ideal choice for the following reasons: 1) Maize is the most abundant crop in the U.S. and can account for a major contribution to cellulosic ethanol, a projected 20 billion gallons. 2) The grain from maize is the principal source of ethanol in the U.S. offering potential cost reduction by synergy with cellulosic and grain ethanol facilities. 3) The grain currently produced for food, feed and fuel accounts for only half of the biomass produced. Applying existing infrastructure for the production of grain to the unused portion of the crop can provide a source of cellulose with no additional inputs required for the fuel crop. 4) Maize is one of the best studied plants and a vast amount of genetics and molecular knowledge is available including characterized variants from both transgenic and more traditional approaches. 5) There have been many studies specifically on the deconstruction of cell walls in maize and maize is one of the targeted cellulosic crops by NREL.

The inventors have found that the enzymatic and synergistic activity can also be found in the germ or endosperm fraction of corn. Since germ is separated from the starch fraction (endosperm) prior to fermentation in many ethanol facilities, there will be no drain on the conversion of starch to ethanol and these enzymes can be provided with no additional input cost or large capital outlay for fermentation facilities. In tests, the amount of germ tissue required is relatively small and preliminary cost estimates indicate that the cost of adding the germ to double the activity of a microbial mixture can be less than the current cost of microbial preparations. These native proteins can be combined with microbial preparations or with engineered maize lines that have developed that contain high levels of cellulase enzymes in the germ or stover that may further aid in the breakdown of cellulose thus requiring less of an enzyme load. In an embodiment the process can be further enhanced when combined with a process that expresses the endocellulase, exocellulase, β-D glucosidases or a combination in the same plant seed which is added to the cellulose-containing composition. Such a process is described in detail at US patent publication No. 20060026715, incorporated herein by reference. When expressing the endocellulase, exocellulase, glucosidase or a combination in plant seed, added expense of purchasing the enzyme is not required, even further reducing costs.

Still further, where the germ is used directly as a source of cellulase and/or to enhance cellulase activity, without the added extraction step, discussed infra, costs will be yet further reduced. The extraction step costs are avoided along with loss of material, estimated to result in a cost about 2 to 2.5 times less than preparing the extract. Transportation and storage costs are likewise reduced. What is more, glucose "credits" can also be captured. As is shown here, the germ itself produces additional glucose, and the tissue thus contributes both cellulase and/or cellulase activity enhancement, as well as additional cellulose. Approximately 60% of dry defatted germ contains carbohydrates potentially convertible to glucose. Ingle et al. (1965) "Changes in composition during development and maturation of maize seeds" *Plant Physiology* 40 (5), 835-839; See, "Typical Composition of Yellow Dent Corn" by Bunge North America, of Bunge Limited at: www.bungenorthamerica.com/news/pubs/03_Bunge_Milling_Process_Diagram.pdf (2011).

It is here shown that glucose production is enhanced. In one embodiment, amylase and xylanase are added to enhance glucose release, in another endogenous amylase and xylanase are expected to enhance glucose release. Therefore using defatted germ would provide a credit rather than a cost. Assuming 88% conversion efficiency to glucose, the cost of the cellulase would be offset by the glucose credits. Germ can be used as the cellulose feedstock source, in which case it provides advantages in that it contains no lignins, and thus needs no pretreatment of what would otherwise be a byproduct. Germ tissue comprising a transgenically produced cellulase, such as E1 and/or CBH1 could be used without the need to add any other enzymes. The germ tissue in another embodiment could be combined with other feedstock, such as wood or stover.

The inventors have shown the synergistic activity provided by the plant tissue. As such, it has been found desirable in one embodiment to maintain the plant tissue used as the source of and/or which enhances cellulase activity at a temperature such that the cellulase providing or cellulase enhancing component is not destroyed or reduced. When exposed to a temperature of 120° C. for 15 minutes, this activity was destroyed. Thus during the process of producing the fermentable sugar, it is desired in an embodiment to assure the plant tissue is not exposed to such conditions. In an embodiment it is desirable to maintain the plant tissue at a temperature such that these parameters are not exceeded, though brief exposure to such temperature is not expected to destroy the activity. In a further preferred embodiment, the temperature is maintained at or below 100° C. and in another at or below 80° C. One skilled in the art can readily test for an ideal temperature by the testing methods described herein, where, for example, the plant tissue is exposed to the temperature, and then contacted with cellulose and determination made if glucose is produced, or added to a cellulase mixture with cellulose and resulting fermentable sugars measured. In one embodiment, temperatures were maintained at or below 40° C. Optimum temperature exposure may be determined by one skilled in the art by testing the plant material for retention of the synergistic activity as described herein.

In the ideal fully integrated production system, maize can be grown as a grain and cellulosic ethanol crop with no additional input cost. Cellulosic material and enzymes would be provided by parts of the plant that are not used for grain ethanol alleviating large capital outlays for fermentation facilities and additional inputs for the production of plant biomass. In this ideal system, everything needed would be produced on one site to reduce environmental concerns, reduce the conversion costs associated with enzymes, and conserve our natural resources.

When using a plant, tissue, parts or cells expressing a heterologous cellulose degrading enzyme as the source of an exogenous cellulose degrading enzyme, the plant can be used in a commercial process. When using the seed itself, it can, for example, be made into flour and then applied in the commercial process. Extraction from biomass can be accomplished by known methods. Downstream processing for any production system refers to all unit operations after product synthesis, in this case protein production in transgenic seed (Kusnadi, A. R., Nikolov, Z. L., Howard, J. A., 1997. *Biotechnology and Bioengineering*. 56:473-484). Seed is processed either as whole seed ground into flour, or fractionated and the germ separated from the hulls and endosperm. If germ is used, it is usually defatted using a hexane extraction and the remaining crushed germ ground into a meal or flour. In some cases the germ is used directly in the industrial process or the protein can be extracted (See, e.g. WO 98/39461). Extraction is generally made into aqueous buffers at specific pH to enhance recombinant protein extraction and minimize native seed protein extraction. In an embodiment, defatting at a temperature that reduces or avoids degradation of the endogenous enzymes is desired to optimize enzyme activity. Thus when optionally defatting germ in one embodiment, the germ is defatted such that temperature at or above 120° for longer than 15 minutes is avoided. In a further preferred embodiment the temperature is at or below 100° C. or 80° C. or 40° C. Any ranges between and below these amounts can be employed which does not destroy the synergistic activity. Subsequent protein concentration or purification can follow. In the case of industrial enzymes, concentration through membrane filtration is usually sufficient.

A variety of assays for the presence of heterologous endo-β-1,4-glucanase, cellobiohydrolase and β-D-glucosidase are known in the art which can be used to detect enzyme activity in extracts prepared from callus and seeds of plants having the heterologous protein. See, Coughlan et al. ((1988) *J. Biol. Chem.* 263:16631-16636) and Freer ((1993) *J. Biol. Chem.* 268:9337-9342). In addition, Western analysis and ELISAs can be used to assess protein integrity and expression levels. Individual $T_1$ seeds are screened by the assay of choice for expression of the target protein, in this case the cellulases or β-glucosidase. Plants having homozygous condition of the transgenic construct expressing the cellulase, that is more than one copy of the gene, are expected to have increased expression levels of the enzyme. Expression levels of two to three to four fold or more are expected. While it is shown here that the germplasm used does not adversely impact expression, it is expected that certain germplasm may have higher levels of expression of the enzyme and may also be selected. The individual plants expressing the highest levels of active enzyme are chosen for field studies, which include backcrosses (See "Plant Breeding Methodology" edit. Neal Jensen, John Wile & Sons, Inc. 1988), selection for increased expression and increased seed amounts. As is evident to one skilled in the art, it is possible to use the processes described to produce a biomass of transformed plants, select higher or highest expressing plant(s), and from selected plant(s) produce a further biomass of plants expressing the desired protein at higher levels and thus provide a convenient source of the protein.

A Western analysis is a variation of the Southern analysis technique. With a Southern analysis, DNA is cut with restriction endonucleases and fractionated on an agarose gel to separate the DNA by molecular weight and then transferring to nylon membranes. It is then hybridized with the probe fragment which was radioactively labeled with $^{32}P$ and washed in an SDS solution. In the Western analysis, instead of isolating DNA, the protein of interest is extracted and placed on an acrylamide gel. The protein is then blotted onto a membrane and contacted with a labeling substance. See e.g., Hood et al., "Commercial Production of Avidin from Transgenic Maize; Characterization of Transformants, Production, Processing, Extraction and Purification" *Molecular Breeding* 3:291-306 (1997).

The ELISA or enzyme linked immunoassay has been known since 1971. In general, antigens solubilised in a buffer are coated on a plastic surface. When serum is added, antibodies can attach to the antigen on the solid phase. The presence or absence of these antibodies can be demonstrated when conjugated to an enzyme. Adding the appropriate substrate will detect the amount of bound conjugate which can be quantified. A common ELISA assay is one which uses biotinylated anti-(protein) polyclonal antibodies and an alkaline phosphatase conjugate. For example, an ELISA used for quantitative determination of laccase levels can be an antibody sandwich assay, which utilizes polyclonal rabbit antibodies obtained commercially. The antibody is conjugated to alkaline phosphatases for detection. In another example, an ELISA assay to detect trypsin or trypsinogen uses biotinylated anti-trypsin or anti-trypsinogen polyclonal antibodies and a streptavidin-alkaline phosphatase conjugate.

An initial test of enzymatic function in one embodiment is performed with lines of processed corn seed. For saccharification of cellulose, plant tissue from these lines are mixed in the appropriate ratio to produce a high specific activity for degradation of crystalline cellulose. According to Baker et al. ((1995) "Synergism between purified bacterial and fungal cellulases", in *Enzymatic Degradation of Insoluble Carbohydrates*. ACS Series 618, American Chemical Society, Washington, D.C., pp. 113-141), in an embodiment, maximum synergism for saccharification of cellulose is with a composite that is about 80% of the *Trichoderma reesei* CBHI (exo-β-1,4-glucanase) and about 20% of the *Acidothermus cellulolyticus* endo-β-1,4-glucanase. The addition of about 0.1% of the *Candida wickerhamii* β-D-glucosidase facilitates the degradation of short glucose oligomers (dp=2-6) to yield glucose. In transgenic enzyme production, later, cross pollination of the selected lines can be used to produce lines that express all three of the cellulase-degrading enzymes or these different enzymes can be engineered into one construct which in turn is transformed into the plant.

Free sugar release can be measured in any convenient manner. One method uses the microbial assay discussed below. This method is automated and allows for real time analysis of different feedstocks enabling determination of the rate of digestion over time. Samples can also be subjected to chemical analysis using HPLC methods and concentrations of specific sugars can be determined. Selected samples can be subjected to microscopic analysis using field emission scanning electron microscopy and antibody labeling with confocal microscopy to determine the effect of digestion. Several different assay methods have been previously reviewed (Ghose, 1987; Zhang et al., 2006; Sharrock, 1988, *Pure Appl. Chem.* 59:257-268). Other methods involve the use of filter paper as the source of cellulose and changes in viscosity measured to detect release of free sugars. Another method relies on chemical analysis to detect the release of free sugars from cellulose (Selig, 2008, Enzymatic Saccharification of Lignocellulosic Biomass Laboratory Analytical Procedure (LAP) www.nrel.gov/biomass/pdfs/42629.pdf). The potential for high throughput enzyme assays (Canevascini and Gattlen, 1981, *Biotechnology and Bioengineering* 23; Glasser et al., 1994; Huang and Tang, 1976, *Biotechnology Progress* 10) and immunochemical assays (Kolbe and Kubicek, 1990, *Applied Microbiology and Biotechnology* 34:26-30) have been developed. Alternative assay methods have been developed to better utilize filter paper (Xiao et al., 2004 *Biotechnology and Bioengineering* 88:832-837) or to incorporate dyes into a cellulosic substrate and monitor their release (Schmidt and Kebernik; Teather and Wood, 1982, *Biotechnology Techniques* 2:153-158). Gel electrophoresis has also been used to identify the enzymes involved (Béguin, 1983, *FEMS Microbial Rev.* 13:25-58). Microbes have been used to evaluate the digestion of cellulose by identification of colonies on agar plates, (Montenecourt and Eveleigh, 1977 *Applied and Environmental Microbiology* 34:777-782).

In a preferred embodiment of the invention and as also described at Methods for Cost-Effective Saccharification of Lignocelluosic Biomass, US publication no. 2003-0109011, both corn seeds and corn stover are harvested by a single harvesting operation. Such a procedure allows for the cost-effective recovery of both the seeds and the stover in one pass through the field. Using this procedure the seeds are collected in a first container and the corn stover in a second container and the collection of both the seeds and the stover is carried out concurrently in a single step. Single pass harvest integrates the collection of the cellulosic biomass with normal crop harvest operations. With this procedure the crop residues are collected without incurring a significant additional cost to the cost of harvesting the corn crop and without causing any additional soil compaction to cultivated fields from the passage of farm machinery, with decreased time and overall costs. Such a process has been demonstrated by Quick, G. R. (Oct. 29, 2001) Corn Stover Harvesting Field Demonstration and Biomass Harvesting Colloquium, Harlan, Iowa (record and minutes of program). In this particular process an IH 1460 with a John Deere 653A row crop head was coupled to a Hesston Stakhand wagon. The machines were modified by the Iowa State Agriculture Engineering department so that two crop streams were provided. Grain was taken up into the combine bin, and whole stover with cobs collected out the back of the machine and conveyed into the Stakhand wagon. This is just one example of the type of machine that can be used in such single pass harvesting.

Following harvest, the kernels can be milled either by the wet or dry milling methods that are known in the art. In one embodiment, germ may be separated from seed and when the germ is to be separated from the seed, to be practical in this process, the germ should be capable of being separated in a commercial milling process, that is a process which does not require hand separation, but can be carried out in a commercial operation. Corn seed, for example, is readily separated from the germ or embryo, where soybean embryos are of a size that the only option for separation is by hand. In instances where the only means of separation of germ is by hand, the process would not be as advantageous from a cost perspective.

There are two major milling processes for corn. Dry milling of corn separates the germ from the endosperm. The endosperm is recovered in the form of coarse grit and corn flakes, or it may be passed through fine rollers and reduced to corn flour.

The bulk of the corn starch produced in the United States is prepared by the wet-milling process. The first step in the wet-milling process is to steep the corn kernels in an aqueous solution. Steeping the kernels serves two main purposes. First it softens the kernels for subsequent milling, and second, it allows undesired soluble proteins, peptides, minerals and other components to be extracted from the kernels. After steeping, the kernels are separated from the steep water and then wet milled. The steep water is typically concentrated by evaporation to yield a solution referred to as a corn steep liquor. Corn steep liquor typically contains about 3.5 pounds dry solids per bushel of corn kernels with a nitrogen content between 45-48% (Blanchard (1992) *Technology of Corn Wet Milling and Associated Processes*, Elsevier, N.Y.

Dry milling does not use the steeping process. The procedure can include, for example, tempering cleaned corn kernels with water or steam to bring them up to 20 to 22% moisture and the corn is then held for about one to three hours. A degerminator or impact mill is used to break open the corn. Discharge from the degerminator is dried to about 15% to 18% moisture. The germ and endosperm are separated by size and/or density, resulting in an enriched fraction for germ or endosperm. See, e.g., Watson, S., Chapter 15, "Corn Marketing, Processing and Utilityzation" pp. 918-923, *Corn and Corn Improvement*, Eds. G. F. Sprague and J. W. Dudley, American Soc. of Agronomy, Crop Society of America, Soil Society of America, Madison, Wis. (1988).

While the invention does not depend on the use of either dry or wet milling, it is recognized that either milling method can be used to separate the germ from the endosperm. In the instance in which transgenic seed expressing one of the enzymes is used under the control of an embryo-preferred promoter, these enzymes can be preferentially produced in the corn germ. Thus, the isolated germ can be used as a source of the substitute for enzymes, or a source of expressed enzymes for cell wall polysaccharide degradation, and the starch-laden endosperm can be utilized for other purposes. If desired, oil can also be extracted from the germ, using solvents such as, for example, hexane, before the germ is contacted with corn stover. Methods for extracting oil from corn germ are known in the art.

With milling, the desired polysaccharide-degrading enzymes can be separated from the starch. As described above, a promoter that drives expression in an embryo, particularly a promoter that preferentially drives expression in the corn germ, can be operably linked to a nucleotide sequence encoding a polysaccharide-degrading enzyme of the invention. Because the germ is separated from the starch during milling, the germ, can in an embodiment be used as the enzyme substitute or enzyme source for degradation of cell wall polysaccharides in the corn stover. While the corn starch can be used for any purpose or in any process known in the art, the starch can also be used for the production of ethanol by methods known in the art. Although the methods of the invention can be used for the saccharification of plant cell wall polysaccharides in any of the processes in which saccharification is desired, such as animal feed additives, gene treatment, and preferably, in the subsequent fermentation into ethanol, the invention does not depend on the production of ethanol. The invention encompasses any fermentative method known in the art that can utilize the fermentable sugars that are produced as disclosed herein. Such fermentative methods also include, but are not limited to those methods that can be used to produce lactic acid, malonic acid and succinic acid. Such organic acids can be used as precursors for the synthesis of a variety of chemical products that can be used as replacements for similar products that are currently produced by petroleum-based methods. See, United States Department of Energy Fact Sheets DOE99-IOFC17 (1999), DOE99-IOFC21 (1999), and DOE/GO-102001-1458 (2001).

Following the degradation or saccharification of cell wall polysaccharides, the fermentable sugars that result therefrom can be converted into ethanol via fermentation methods employing microorganisms, particularly yeasts and/or bacteria. Such microorganisms and methods of their use in ethanol production are known in the art. See, Sheehan 2001. "The road to Bioethanol: A strategic Perspective of the US Department of Energy's National Ethanol Program" In: Glucosyl Hydrolases For Biomass Conversion. ACS Symposium Series 769. American Chemical Society, Washington, D.C. Existing ethanol production methods that utilize corn grain as the biomass typically involve the use of yeast, particularly strains of *Saccharomyces cerevisiae*. Such strains can be utilized in the methods of the invention. While such strains may be preferred for the production of ethanol from glucose that is derived from the degradation of cellulose and/or starch, the methods of the present invention do not depend on the use of a particular microorganism, or of a strain thereof, or of any particular combination of said microorganisms and said strains.

Furthermore, it is recognized that the strains of *Saccharomyces cerevisiae* that are typically utilized in fermentative ethanol production from corn starch might not be able to utilize galacturonic acid and pentose sugars such as, for example, xylose and arabinose. However, strains of microorganisms are known in the art that are capable of fermenting these molecules into ethanol. For example, recombinant *Saccharomyces* strains have been produced that are capable of simultaneously fermenting glucose and xylose to ethanol. See, U.S. Pat. No. 5,789,210, herein incorporated by reference. Similarly, a recombinant *Zymomonas mobilis* strain has been produced that is capable of simultaneously fermenting glucose, xylose and arabinose to produce ethanol. See, U.S. Pat. No. 5,843,760; herein incorporated by reference. See, also U.S. Pat. Nos. 4,731,329, 4,812,410, 4,816,399, and 4,876,196, all of which are herein incorporated by reference. These patents disclose the use of *Z. mobilis* for the production of industrial ethanol from glucose-based feedstocks. Finally, a recombinant *Escherichia coli* strain has been disclosed that is able to convert pure galacturonic acid to ethanol with minimal acetate production. See, Doran et al. ((2000) *Appl. Biochem. Biotechnol.* 84-86:141-152); herein incorporated by reference.

When referring to a plant tissue composition is meant any plant part, plant tissue (which can be optionally ground, sieved, pulverized, chopped, sliced, minced, ground, crushed, mashed or soaked or the like as long as the cellulose degradation enhancing property is retained) or extract, and it is not required to identify or purify a single cellulase protein. Further, it is not meant to imply the entire plant must be used or that plant tissue or cells must be present in the composition in the final extract where an extract is provided as long as plant cells are used to produce the extract. Any plant tissue composition can be used in the invention, whether the tissue composition is not transformed with a nucleic acid molecule expressing a cellulose degrading enzyme, and/or where plant tissue is transformed to express a cellulose degrading enzyme such as an endocellulase, or exocellulase, or β-D glucosidase or combination and thus provides a source of exogenous cellulase or β-D glucosidase. The tissue composition enhances the activity of any exogenous cellulase used in the process, and is particularly useful when employed with a commercially available "cocktail" composition of any desired combination of exogenous enzymes. For example, plant seed, leaves, roots, stem or other plant parts and tissue of plant parts and extracts of same can be employed in an embodiment of the invention. In one preferred embodiment the tissue composition is seed tissue composition. Such plant seed tissue can include the whole seed or its parts, including pericarp (kernel or hull), embryo (called the germ in processing language), or endosperm. In a preferred embodiment, the plant tissue is embryo plant tissue or extract. The plant seed tissue may be in another embodiment a grain seed or part thereof. In yet another embodiment, the plant tissue is a corn seed tissue or part thereof, such as, for example, an embryo that is also referred to as the germ. When referring to tissue is meant an aggregate of cells that can constitute structure(s) or component(s) of the plant, or which can be a portion of such structure or component, or which are from more than one such structure or organ. Seed tissue can be whole seed, portions of the seed, and ground or pulverized or otherwise processed in a manner that is convenient. The tissue composition in one embodiment can be a suspension of plant cells. As has been noted, whole plant may be used where convenient for the process, though one may desire to instead use other plant parts for other profitable uses.

The tissue composition can also be provided as an extract. While it may be convenient to provide tissue in the form of plant parts, whole seed or seed components, for example, one may also prepare flour or the like, there may be instances in which use of an extract is desired. Any of the many available means to prepare such an extract can be employed. When referring to an extract is meant the general process of placing tissue/cells in a liquid, preferably a buffer (the tissue may be optionally ground or otherwise pre-treated), and removing the supernatant. The inventors have found it is not necessary to identify and purify a single protein from the plant. Rather, when referring to an extract here, is meant placing tissue in the liquid, without the need to purify a single protein. In examples below, the supernatant may be further passed through a desalting column to separate high molecular weight from low molecular weight compounds, and the high molecular weight fraction used. This was employed for experimental purposes, since the low molecular weight portion would contain glucose and high molecular weight the protein, and it was desired to assure the experimentation with yeast did not contain significant amounts of glucose from the tissue. However, in a commercial situation, the presence of glucose could be highly desirable. Thus one can prepare an extract in those situations where it is convenient to do so, by simple placing tissue in a liquid. A person skilled in the art could test any such extract for use in the invention by determining if it provides the increase in fermentable sugars and/or synergist result found here. For example, one may test the extract by determining if it increases production of fermentable sugars from cellulose when added with a combination of endocellulase, exocellulase and β-D glucosidase (such as, for example, the commercially available Spezyme® composition) and determining if release of fermentable sugars is at least 25% higher compared to the same process where the extract is not added. Further, one could test to determine if fermentable sugars are released when the extract is combined with cellulose, with reduced amounts of cellulase, or with no additional β-D glucosidase added. In another embodiment, one could test to determine if glucose is produced when the extract is combined with cellulose and no additional cellulase or β-D glucosidase is added.

The cellulosic biomass can originate from the same plants as the plant tissue or from different plants. Preferably, the cellulosic biomass comprises plant residues. More preferably, in one embodiment, the cellulosic biomass comprises crop residues normally left in the field after the harvest of corn grain, which is also known as corn stover. Most preferably, the cellulosic biomass comprises corn stover that is from the same plants as the cell wall polysaccharide-degrading enzyme substitute and/or enzymes for increased cost efficiency.

In certain embodiments of the invention, it may be desired to process the plant tissue so as to produce an extract and then contacting the cellulosic biomass with the extract. The processing of the plant tissue to prepare such an extract can be accomplished as described supra, or by any method known in the art for the extraction of an enzyme from plant tissue. In other embodiments of the invention, the plant tissue and the cellulosic biomass may be combined and then processed as described supra. See, e.g., Henry & Orit (1989) Anal. Biochem. 114:92-96.

The cellulose composition, also referred to as the cellulosic biomass is contacted with the plant tissue composition and may also include in the process a cellulase and/or β-D glucosidase, and exposed to conditions favorable for the degradation of the polysaccharides in the cellulosic biomass. When referring to adding an enzyme or adding plant tissue composition is not meant to imply any particular series of steps, as the enzyme or tissue composition can be placed in contact with the cellulosic biomass in sequence, several at one time, others at a later time, at the same time or in any manner convenient to the system used. Both extract and tissue can be utilized where desired. Clearly, one could employ one source of plant tissue composition as the contributor of the enzyme substitute, and another as contributor of the transgenically expressed enzyme, or both can be provided in one plant tissue composition. Prior to contacting the cellulosic biomass with the plant tissue composition, the plant tissue composition or the cellulosic biomass, or both, can be pretreated or processed in any manner known in the art that would enhance the degradation of the polysaccharides. For example, the cellulosic biomass can be processed by being chopped, sliced, minced, ground, pulverized, crushed, mashed or soaked. Such processing can also include incubating the plant tissue and/or cellulosic biomass in a solution, particularly an aqueous solution. If desired, the solution can be agitated, mixed, or stirred. The solution can comprise any components known in the art that would favor extraction of an active enzyme from the plant tissue and/or enhance the degradation of cell wall polysaccharides in the cellulosic biomass. Such components include, but are not limited to, salts, acids, bases, chelators, detergents, antioxidants, polyvinylpyrrolidone (PVP), polyvinylpolypyrrolidone (PVPP), and $SO_2$. Furthermore, specific environmental conditions, such as, for example, temperature, pressure, pH, $O_2$ concentration, $CO_2$ concentration, and ionic strength, can be controlled during any processing and/or subsequent steps to enhance polysaccharide degradation and/or ethanol production. In yet another embodiment of the invention, prior to contacting the cellulosic biomass with the plant tissue composition thereof, the cellulosic biomass can be prepared by pretreating the cellulosic biomass by methods known in the art (Nguyen et al. 1996. NREL/DOE Ethanol Pilot Plant Current Status and Capabilities. Bioresource Technology 58:189-196). In one pretreatment step, the hemicellulosic fraction of the feedstock is hydrolyzed to soluble sugars. This step also increases the enzyme's ability to convert the major fraction of the feedstock (cellulose) to soluble glucose. The pretreatment step mixes the feedstock with sulfuric acid and water (approximately 1% acid in the final solution), then raises the slurry (20-25% solids) to reaction temperature (160-200° C.) with steam. The mixture is held at the reaction temperature for a predetermined time (2-20 min) then flashed into a tank maintained at near atmospheric pressure. Because of the sudden pressure drop, a fraction of the steam condensate and volatile compounds formed during the heating is evaporated and removed as flash tank overhead, which is condensed and sent to waste treatment. Lime is added to the remaining slurry to adjust the pH to 4.5. As discussed herein, pretreatment to reduce or remove lignin has been found to be unnecessary where germ is used as the source of cellulose.

While the cell wall polysaccharides are degraded prior to utilization of the fermentable sugars by microorganisms, the methods are not limited to a saccharification step which precedes the fermentation step for example. In certain embodiments of the invention, a single combined saccharification/fermentation step can be employed in the methods of the invention. In other embodiments, saccharification is initiated before fermentation and can be fully or partially complete prior to the initiation of the fermentation.

The following illustrates, but is not intended to limit the scope of the invention. It will be evident to one skilled in the art that variations and modifications are possible and fall within the scope and spirit of the invention.

Example 1

The following describes one method useful in measuring fermentable sugars released from cellulosic feedstock and materials, methods and procedures used in the following examples. This method uses a commercially available device, called BacT/ALERT® produced by bioMérieux (see www.biomerieux-diagnostics.com). This device provides colorimetric real time detection of $CO_2$ released by bacteria and pH changes for early detection of microorganisms in a clinical setting. In this instance, the device is useful in monitoring $CO_2$ released by yeast which grow on the glucose resulting from fermentable sugars produced with breakdown of cellulose over time. The process is automated and can follow the course of the reactions in real-time in a non-destructive manner allowing for intervention of the assay at any point. In addition, the BacT/ALERT® verifies that the reaction products are compatible with microbial growth.

Materials and Methods
Microbial Growth:

100 mg of Fleischmann's® RapidRise quick-acting yeast were allowed to grow 4-6 hours in 5 mL of yeast broth; 0.1 ml was used to inoculate the BacT/ALERT® bottles in a laminar flow hood. Cellulose was autoclaved (0.025 g/mL in 140 mM citrate/90 mM bicarbonate buffer pH5). Ten mL were added to each bottle along with 30 mL of buffer for a total volume of 40 mL per bottle. Cellulase was added last to the BacT/ALERT® bottle. The bottle top was wrapped with parafilm, and 180 mL of atmosphere was removed with a syringe. While in the instrument, the bottles are incubated at 37.5° C., rocked at approximately 70 rocks per minute and monitored every 10 minutes for a color change. The sensor is made to detect changes in $CO_2$ production, as well as other organic and inorganic acids and pH change.

Cellulose Substrates:

The sources of cellulose used were Sigmacell (Sigma-Aldrich® Chemical Co., St. Louis, Mo.), 1 mm×1 mm pieces of Whatman paper #1, pretreated rice hulls (FutureFuel™ Chemical Company (FFCC), Batesville, Ark.), and pretreated hardwood (FFCC). For each experiment, 0.25 g of cellulose in 10 mL of buffer was vortexed for 1 minute to dissolve the cellulose and the contents were then added to a BacT bottle.

Enzyme Activity:

Cellulase assays were done as described earlier (Hood et al., 2007, *Plant Biotechnology Journal* 5:709-719). All reactions were carried out at 50° C. using *T. reseei* (Sigma # C8546) as the standard. Carbohydrate concentrations were obtained using protocols established by the National Renewable Energy Laboratory Technical Report, NREL/TP-510-42623 (nrel.gov/biomass/pdfs/42623.pdf). Analysis was performed on a Shimadzu Prominence Series HPLC with a Bio-Rad Aminex (HPX-87P) column, a Bio-Rad dewashing precolumn and an Agilent 1200 Series Refractive Index Detector. Results shown are the median of three replicate samples.

Results

Figure 2:
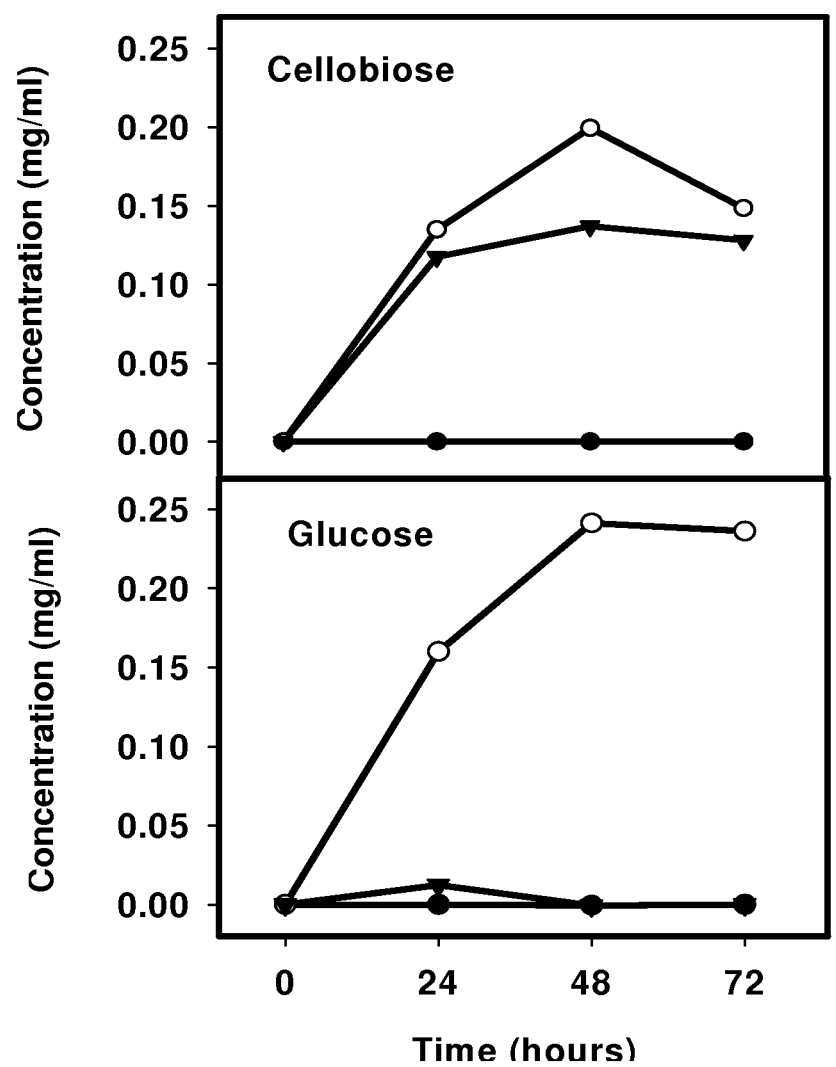
FIG. 2 is a graph showing HPLC detection of cellobiose or glucose over time produced when cellulose is combined with cellulase (open circles) or in where cellulose is combined with cellulase and yeast (triangles) or where only cellulose was present (closed circles).

It was first necessary to establish a baseline of the growth pattern of microbes using the BacT/ALERT® system. Samples were prepared as described in the Materials and Methods section and supplemented with glucose to obtain an optimal growth pattern for yeast. FIG. 1 (line A) shows a typical response over time where most of the growth occurs within the first 40 hours (2400 minutes). When glucose is absent and the only carbon source is cellulose supplemented with a cocktail of enzymes known to digest cellulose the growth approaches that of the yeast grown on glucose (line B). When yeast is grown only with the enzyme but no cellulose (line C), with cellulose but no enzymes (line D) or without cellulose or enzymes (line E) only a very small amount of growth can be seen in the first few hours that is most likely due the residual sugar from the yeast starter culture used in the inoculation. After the first four hours, these latter treatments show little or no growth. Treatments that do not have yeast but contain either cellulose or enzymes (line F) or enzymes alone (line G) show the predicted baseline values with no growth. This shows a qualitative method of evaluating the release of free sugars. Aliquots from treatments as described above were sampled at various times and prepared for HPLC. The results reveal that in the presence of a mixture of cellulase enzymes, cellobiose and glucose (FIG. 2, open circles) are released as expected over time. In the absence of cellulase (closed circles), no sugars are released. Samples containing no cellulose but including yeast (triangles) were also analyzed by HPLC which revealed the presence of cellobiose but almost no glucose. Presumably the yeast is utilizing the glucose but not cellobiose. No other sugars were detected above a concentration of 0.01 mg/ml.

Figure 3A:
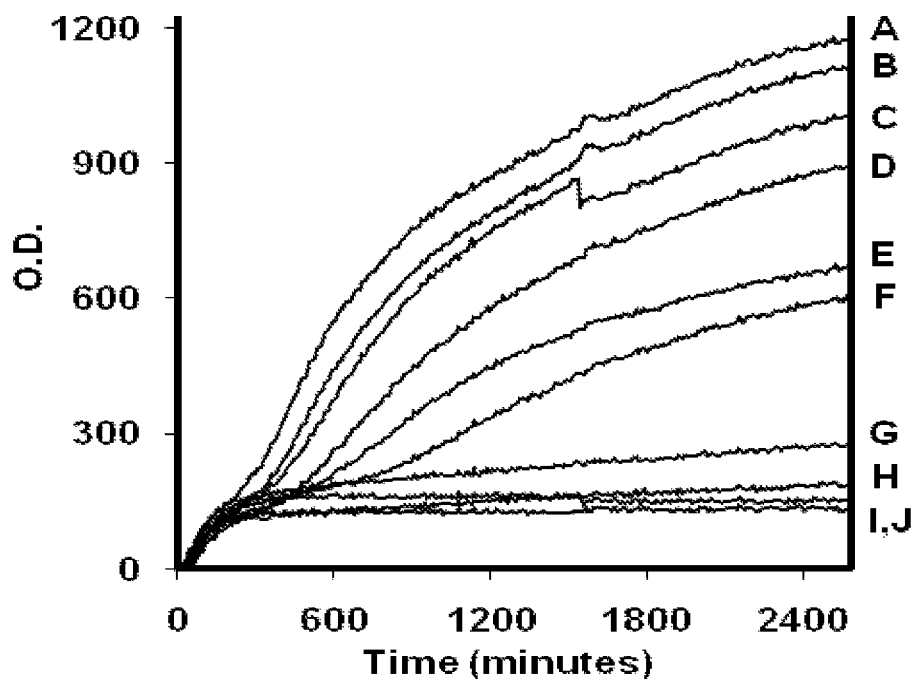
FIG. 3 shows graphs measuring color change correlated with yeast growth or rate of growth when a combination enzyme preparation is added at various concentrations. At 3A optical density is shown over a forty-hour period or at 3B over a twenty-hour period with different concentrations of a composition containing endocellulase, exocellulase and β-D glucuronidase.
FIG. 3C shows rate (top of graph) and final OD (bottom graph) over time.
Figure 3B:
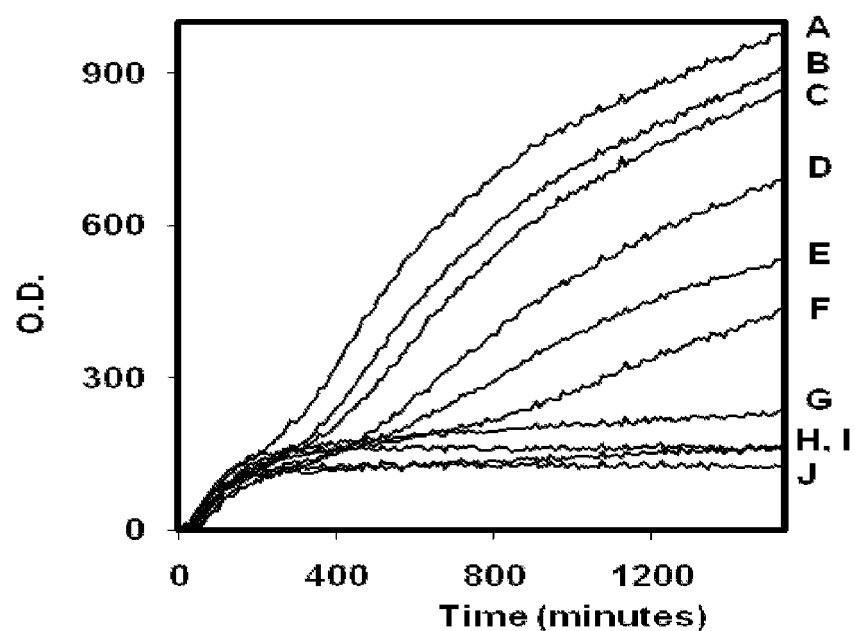
Figure 3C:
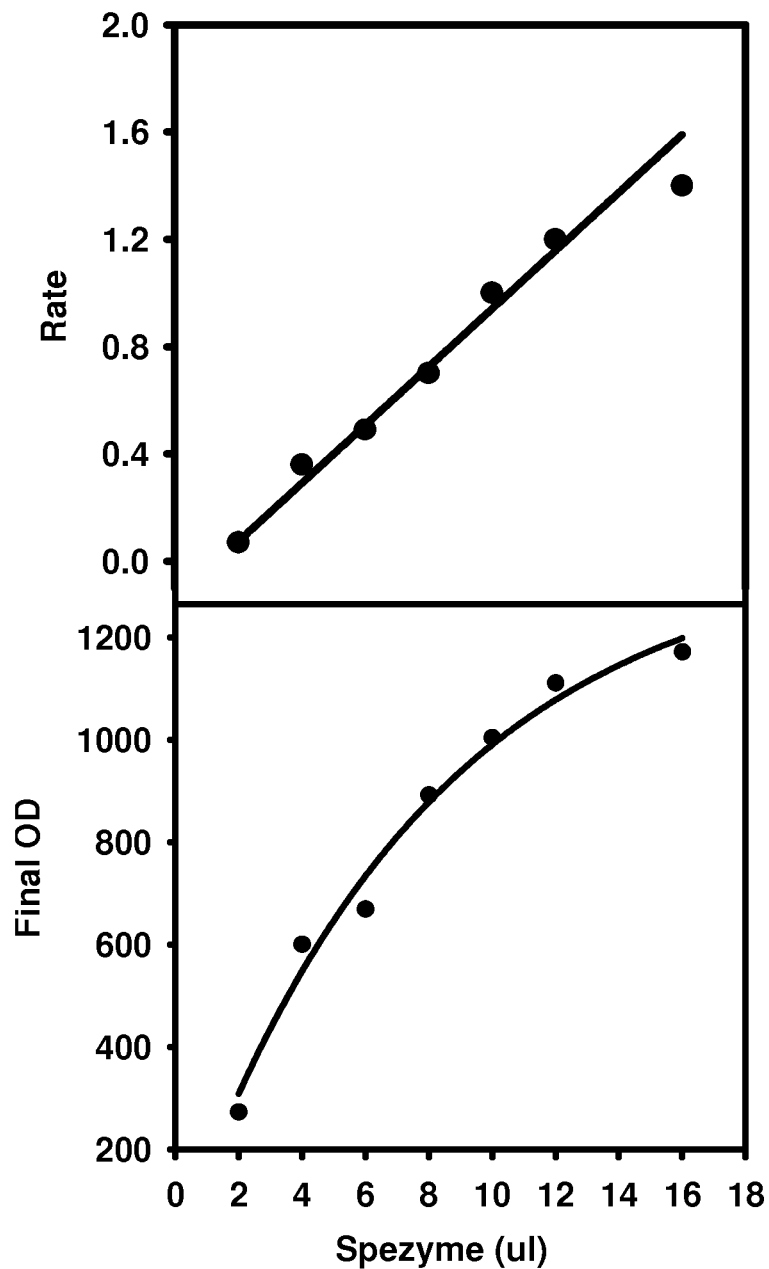

A combination enzyme composition containing endocellulase, exocellulase and β-glucosidase was used. (The commercially available cellulase enzyme mixture, Spezyme® CP is obtainable from Genencor) It was tested at various concentrations to observe the dependence on yeast growth. In FIGS. 3C and D, A-J represents varying concentrations of 2, 4, 5, 8, 10, 12 and 16 µl. In FIGS. 3A and B concentrations of 1, 0.5 and 0 µl are also measured. The yeast growth, results shown as optical density (OD, FIG. 3), appears dependent on enzyme concentration. FIG. 3A shows measurement over 20 hours, FIG. 3B over 40 hours. These data can be also be used to establish a quantitative relationship by examining the final OD after 2 days, or the rate of the reaction during the first 12 hours. Ignoring the first few hours when samples show the carry-over growth from the inoculated yeast cultures, the subsequent linear range can then be used to develop a standard curve and determine the relative activity of unknown samples. In FIG. 3C the graph shows measurement of the rate of growth (top graph) and final OD (bottom graph) at varying concentration of the combination enzyme composition.

Figure 4:
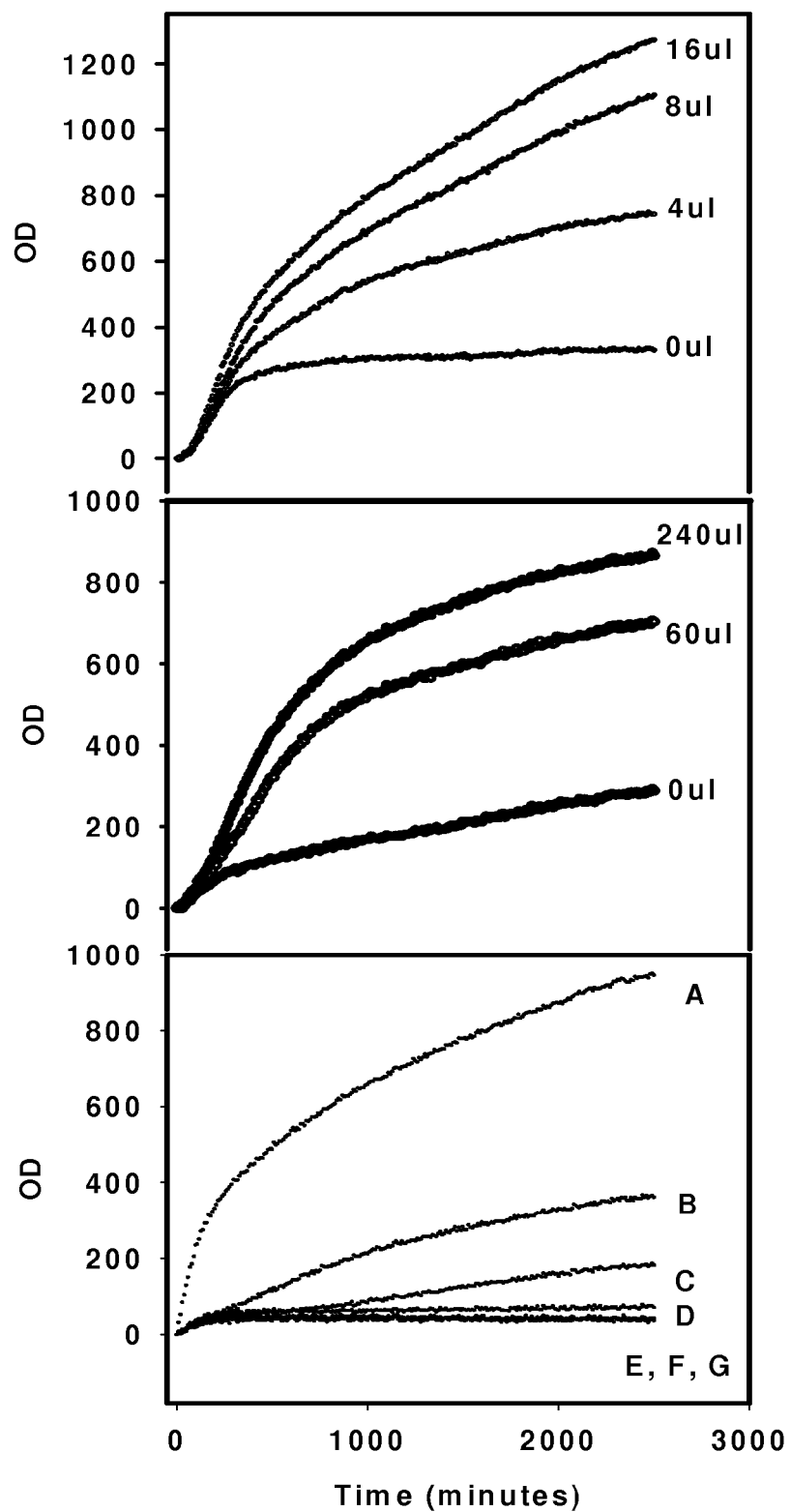
FIG. 4 is a graph measuring color change correlated with yeast growth using various sources of cellulase, from Whatman paper number 1, rice hulls or hardwood, with combination enzyme added at various concentrations. Concentrations are listed in the top graph, and in the bottom graph are 0, 2, 4, & 16 microliters of enzyme.

Different sources of cellulose were also evaluated. This included readily available cellulose sources used in research such as Sigmacell and Whatman paper #1 as well as potential commercial cellulosic ethanol substrates such as pretreated rice hulls and hardwood. FIG. 4 shows the results when these other cellulose sources are treated with enzymes. All of the cellulose sources provided an increase in yeast growth proportional to the amount of enzyme added. The different sources of cellulose required different amounts of enzyme to obtain the same amount of yeast growth. We can obtain an approximation of the concentration that gives 50% digestion ($DC_{50}$) of each type of substrate to estimate the relative digestibility of the cellulose with this specific mixture of enzymes. Sigmacell required the lowest concentration of enzymes to permit yeast growth ($DC_{50}=2$) followed by Whatman paper and hardwood ($DC_{50}=4$). Rice hulls required the highest concentration of enzymes ($DC_{50}=40$). Therefore this method may be used to evaluate the best enzyme cocktails for specific substrates and determine the relative digestibility of different substrates. This may have utility not only for comparing different plant sources but modified lignocellulose from the same plant as has been suggested by others (Sticklen, 2006 *Curr Opin Biotechnol* 17:315-9).

Example 2

Plants were transformed with an endocellulase encoding nucleotide sequence as is described in US Publication No. 20060026715, incorporated herein by reference. In brief, a construct was prepared with an endo-1,4-β-D-glucanase encoding nucleotide sequence (See U.S. Pat. No. 6,573,086) and a seed-preferred promoter PGNpr2 (a maize globulin-1 gene, described by Belanger, F. C. and Kriz, A. L. 1991. Molecular Basis for Allelic Polymorphism of the maize Globulin-1 gene. *Genetics* 129: 863-972, also found as accession number L22344 in the GenBank database), the KDEL endoplasmic reticulum retention sequence (Lys-Asp-Glu-Leu), (see Munro, S, and Pelham, H. R. B. 1987 "A C-terminal signal prevents secretion of luminal ER proteins" *Cell* 48:899-907), the barley alpha-amylase signal sequence, (Rogers, J. C. 1985. Two barley alpha-amylase gene families are regulated differently in aleurone cells. *J. Biol. Chem.* 260: 3731-3738), which was optimized, and a pin II terminator (An et al., 1989. Functional analysis of the 3' control region of the potato wound-inducible proteinase inhibitor II gene. *Plant Cell* 1:115-122). The 35S promoter, (Odell et al. (1985) *Nature* 313:810-812), drives the selectable marker, the maize optimized PAT gene. The gene confers resistance to bialaphos. (See, Gordon-Kamm et al, *The Plant Cell* 2:603 (1990); Uchimiya et al, *Bio/Technology* 11:835 (1993), and Anzai et al, *Mol. Gen. Gen.* 219:492 (1989)). The E1 cellulase gene from *Acidothermus cellulolyticus* was received from NREL. For expression in maize, the first 40 amino acids were optimized to maize preferred codons. The BAASS and KDEL sequences were added to the gene by PCR using the NREL clone as template. The PCR product moved to a PCR-ready cloning vector, then moved to an intermediate vector to add the pin II terminator sequence, and then shuttled into the plant expression vector as a complete unit. PGNpr2 is just upstream of the E1 gene.

Fresh immature zygotic embryos were harvested from Hi-II maize kernels at 1-2 mm in length. The general methods of *Agrobacterium* transformation were used as described by Japan Tobacco, at Ishida et al. 1996. "High efficiency transformation of maize (*Zea mays* L.) mediated by *Agrobacterium tumefaciens*" *Nature Biotechnology* 14:745-750 with some modifications as is described at US publication 20060026715. Fresh embryos were treated with 0.5 ml log phase *Agrobacterium* strains EHA101. Bacteria were grown overnight in a rich medium with kanamycin and spectinomycin to an optical density of 0.5 at 600 nm, pelleted, then re-inoculated in a fresh 10 ml culture. The bacteria were allowed to grow into log phase and were harvested at no more dense than OD600=0.5. The bacterial culture is resuspended in a co-culture medium.

For stable transformations, embryos were transferred to a bialaphos selective agent on embryogenic callus medium and transferred thereafter every two weeks to allow growth of transformed type II callus. Plants were regenerated from the callus. Desalting columns were used to separate high molecular weight from low molecular weight molecules.

Figure 5:
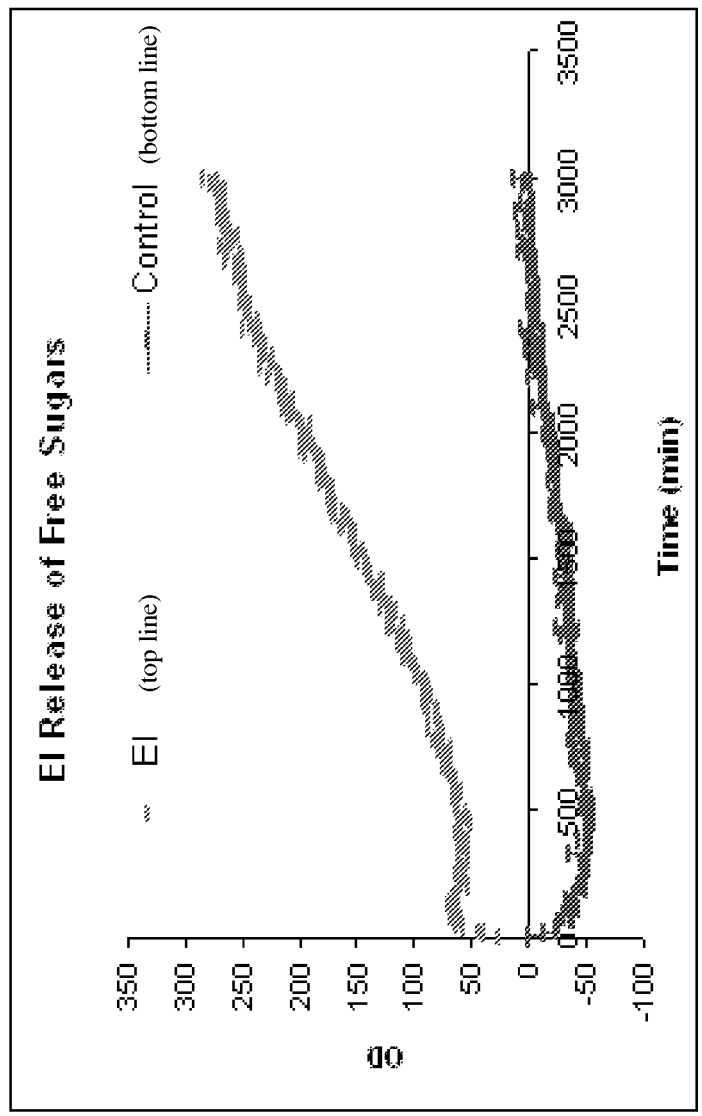
FIG. 5 is a graph showing release of fermentable sugar, as color change correlated with yeast growth, when extract from a plant expressing E1 cellulase was added to cellulose, or when non-transgenic plant extract was added.

Following extraction, the extract was placed in BacT/ALERT® bottles as described in Example 1 and results compared with a control with non-transgenic corn extract. Release of free sugars was measured as described supra, and results shown in FIG. 5. As can be seen from the results, these extracts were able to obtain a complete release of fermental sugars without the addition of any other enzymes.

Example 3

Transgenic maize expressing exocellulase was prepared as described at US Publication No. 20060026715. In brief, the CBH I gene construct was prepared, similar to the E1 construct but in this case having the BAASS sequence only, such that the enzyme is secreted to the cell wall. The starting CBH I clone was received from NREL. It is also known as cbh1-4 from *Phaneorchaete chrysosporium* (the genomic is shown in Gen Bank accession L22656). This gene most closely matches the CBH I gene from *Trichoderma koningii* at the nucleic acid level. The gene was maize optimized for the first 40 amino acids using a PCR based mutagenesis approach—this includes the 24 amino acid BAASS sequence. Codons D346 and D386 were also maize codon optimized to remove the potentially destabilizing sequences at those positions. The BAASS sequence was added to the optimized CBH I gene by PCR. The PCR product was moved to an PCR-ready cloning vector to add the pin II terminator, and then the whole unit was transferred to the transformation vector. The promoter PGNpr2 is used to drive the transcription of CBH I coding sequence. Transformation of maize proceeded as described supra. Seed extract was obtained as described in extracting the E1 endocellulase. The material as described below were placed in BacT/ALERT® bottles as described by the methods of Example 1 and in Example 2.

Figure 6:
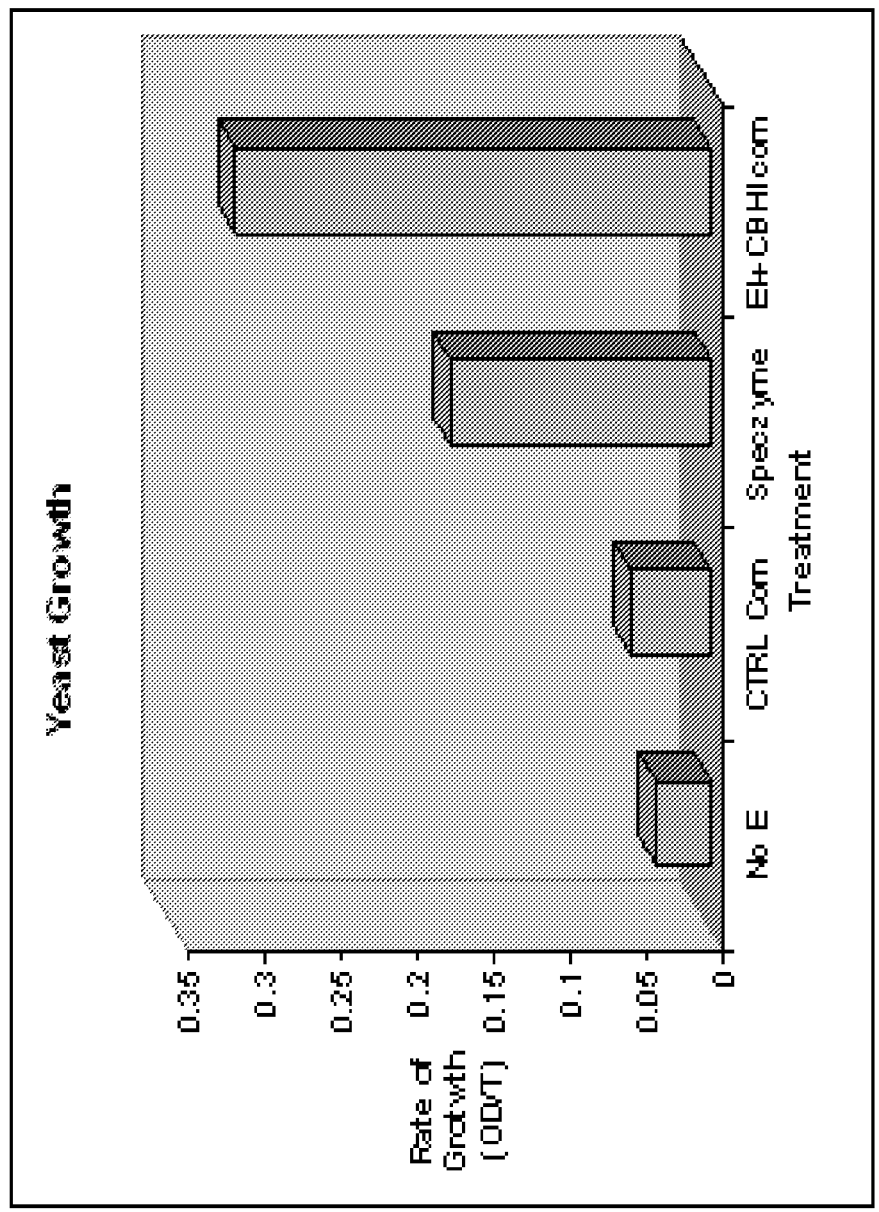
FIG. 6 is a graph showing release of fermentable sugar, as color change correlated with the rate of yeast growth, when no cellulase is included with cellulose ("No E"); when non-transgenic corn is added ("CTRL corn"); when a commercial enzyme preparation is added and when corn expressing E1 endocellulase and corn expressing CBHI exocellulase is added ("E1+CBHI corn").

In a first treatment, no plant material and no enzymes were added, in the second treatment, seed extract alone was added, in the third treatment commercial enzyme containing endocellulase, exocellulase and glucosidase was added, and in the fourth treatment, seed extract from the transgenic E1 corn and transgenic CBHI corn was added. The results are graphed in FIG. 6. As can been seen from the results, the seed extracts from corn expressing the enzymes provides a complete reaction and a dramatic increase in release of fermentable sugars compared to addition of enzymes without plant material.

Example 4

Figure 7:
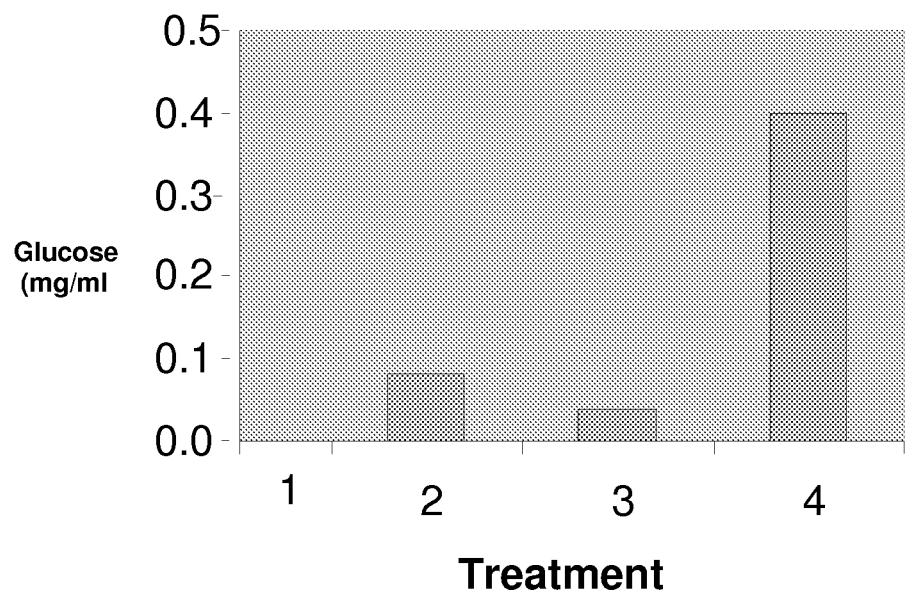
FIG. 7 is a graph showing the measurement of glucose from hardwood, with no additional enzymes (treatment 1), when a commercial preparation of enzymes having endocellulase, exocellulase and β-D glucosidase was added (treatment 2), seed extract alone was added (treatment 3) and combination of the commercial enzyme composition and seed extract was added (treatment 4).

Samples of hardwood were prepared in bottles as described in Example 1. Corn seed extracts were prepared by adding 4 parts of 50 mM acetate buffer pH 5 to 1 gram of ground seed. The extract was passed over a desalting column (e.g. Sephadex G25) and the high molecular weight fractions collected. Chemical analysis of glucose was performed by HPLC. In treatment number 1, no enzyme or seed extracts were added; in treatment number 2, 3 ul of a combination enzyme composition containing endocellulase, exocellulase and glucosidase was added; in treatment 3, 5 ml seed extract alone was added; in treatment 4, a combination of seed extract and the combination enzyme having endocellulase, exocellulase and β-D glucosidase was added. FIG. 7 shows the results and confirms the synergistic effect of adding the seed extract to the combination enzyme preparation.

Rates of growth were also calculated with the seed extract alone, commercial cellulase preparation along and a combination of the two. Sigmacell was used as the cellulose source and methods of measurement used the BacT/ALERT® system as described in Example 1.

TABLE 2

| Sample | Rate |
| --- | --- |
| Seed extract | 0.087 |
| combination cellulase | 0.268 |
| seed extract and combination cellulase | 0.839 |

Figure 8:
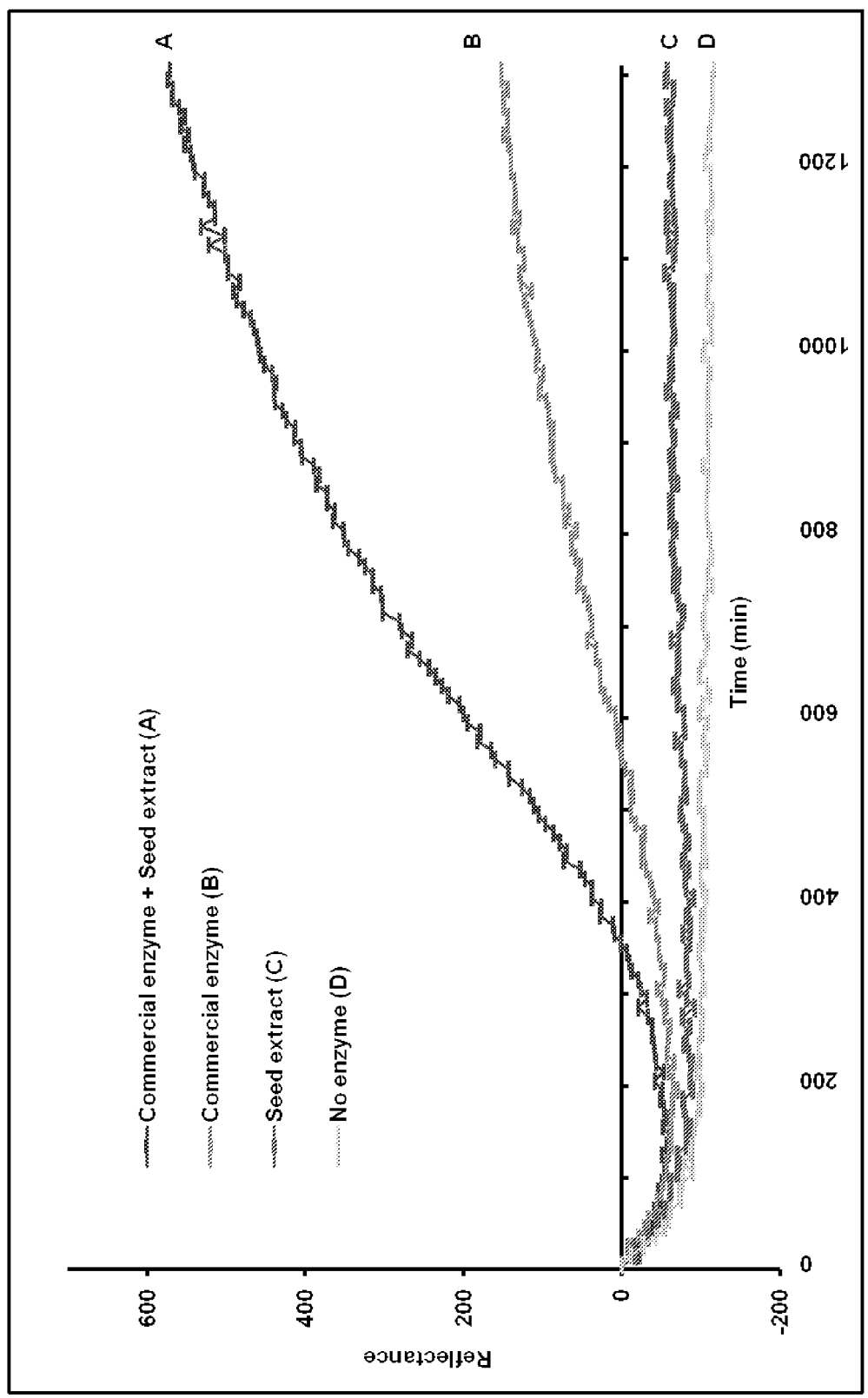
FIG. 8 is a graph showing the release of fermentable sugar when cellulase is combined with (A) a commercial preparation of enzymes having endocellulase exocellulase and β-D glucosidase and seed extract; (B), commercial enzyme alone; (C) seed extract alone; and (D) where no enzyme is added.

Also see FIG. 8, which shows rates of growth measured when commercial cellulase preparation and seed extract is added to cellulose (A), where only commercial enzyme is added (B), where seed extract alone is added (C) and where no enzyme is added (D).

Example 5

Materials and Methods

Materials:

Sigmacell (Sigma Chemical Co., St. Louis, Mo., and pretreated hardwood (obtained from Future Fuels Chemical Company) were used as the sources of cellulose. Celluclast (Novozyme cellulase mixture) was used for all cellulose digestion assays with the exception of those using *Trichoderma reesei* (Sigma # C8546) that was used for in a comparison study and in all biochemical assays.

Tissue Extracts:

Seeds were ground in a coffee grinder into meal and fresh plant tissue was ground using liquid nitrogen in a mortar and pestle. Acetic acid buffer (pH5 50 mM), was added at a ratio of 1 g tissue:5 mls buffer. Extract was stirred and centrifuged at 10,000XG for 10 minutes. The supernatant (CSE) was used as described in results.

Cellulase:

Cellulase enzymatic assays were performed as described earlier (Hood et al. (2007) *Plant Biotechnology Journal* 5:709-719) at 50° C. using *T. reesei* (Sigma # C8546) as the standard to compare enzyme activity.

Free Sugar Analysis:

Free sugar concentrations were measured using protocols established by the National Renewable Energy Laboratory Technical Report, NREL/TP-510-42623 (www.nrel.gov/biomass/pdfs/42623.pdf). Chemical analysis for sugars was performed on a Shimadzu Prominence Series HPLC with a Bio-Rad Aminex (HPX-87P) column, a Bio-Rad de-ashing precolumn and an Agilent 1200 Series Refractive Index Detector.

Glucose Oxidase Assay:

The GLOX assay was conducted as described by the Worthington Biochemical website (www.worthington-biochem.com/gop/assay.html) with the following modifications. Peroxidase and glucose oxidase were resuspended to 1 mg/mL, non-oxygenated o-dianisidine was resuspended in DMSO to a stock concentration of 2% and used in the assay at a concentration of 0.016%, and a 10% D-glucose stock solution was left to mutarotate for a minimum of one hour. The total assay volume was 200 µl uL: 150 µl o-dianisidine solution, 10 µl peroxidase, 10 µl L glucose oxidase, and 30 µl of glucose standard or cellulase reaction sample. The reaction was conducted at room temperature and readings were taken at 460 nm every 30 seconds for 5 minutes. SoftmaxPro5.4 software was used to analyze reaction rates.

Yeast Growth Assay:

Yeast were grown on media containing cellulose as the sole carbon source supplemented with cellulase and monitored for growth as described previously (A novel method for evaluating the release of fermentable sugars from cellulosic biomass. Rafael Jimenez-Flores, Gina Fake, Jennifer Carroll, Elizabeth Hood, John Howard, *Enzyme and Microbial Technology* 47 (2010) 206-211

Results

Figure 9:
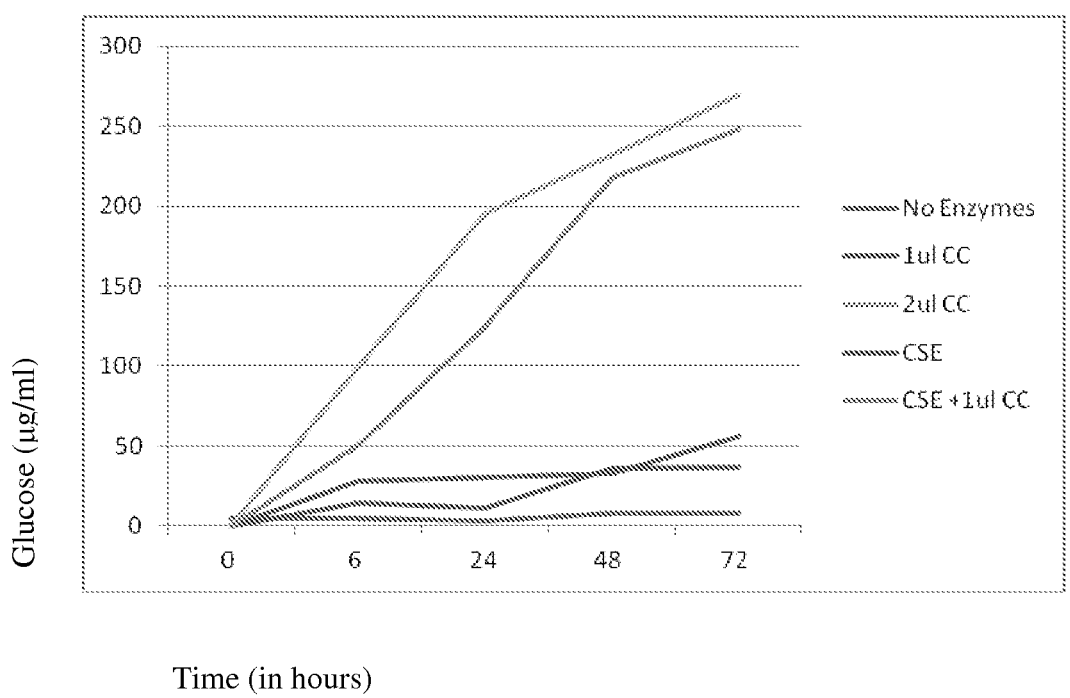
FIG. 9 is a graph showing amount of glucose produced when cellulose was incubated with no enzymes, with varying concentrations of commercial cellulase enzyme compositions (CC) and seed extract (CSE) with and without the microbial cellulase as measured by GLOX.

A commercial preparation of cellulase (Celluclast) was incubated with cellulose (Sigmacel) and glucose measured at selected times to establish a dose curve for cellulase. Concentrations of cellulase that provided significant but non saturating amounts of glucose (between 1-4-ul of Celluclast/100 ul of reaction mixture containing 2 mgcellulose) were used in subsequent experiments. To establish the synergistic effect, the crude seed extract (10 ul/200 ul reaction mixture was then added to cellulose and the release of glucose was measured as described in Materials and Methods. The results shown in FIG. 9 indicate that the glucose released from seed extract (CSE) in the presence of Celluclast (CC) was equivalent to the amount of glucose using twice as much Celluclast. See FIG. 9, which shows glucose measured in micrograms/ml over time.

Figure 11:
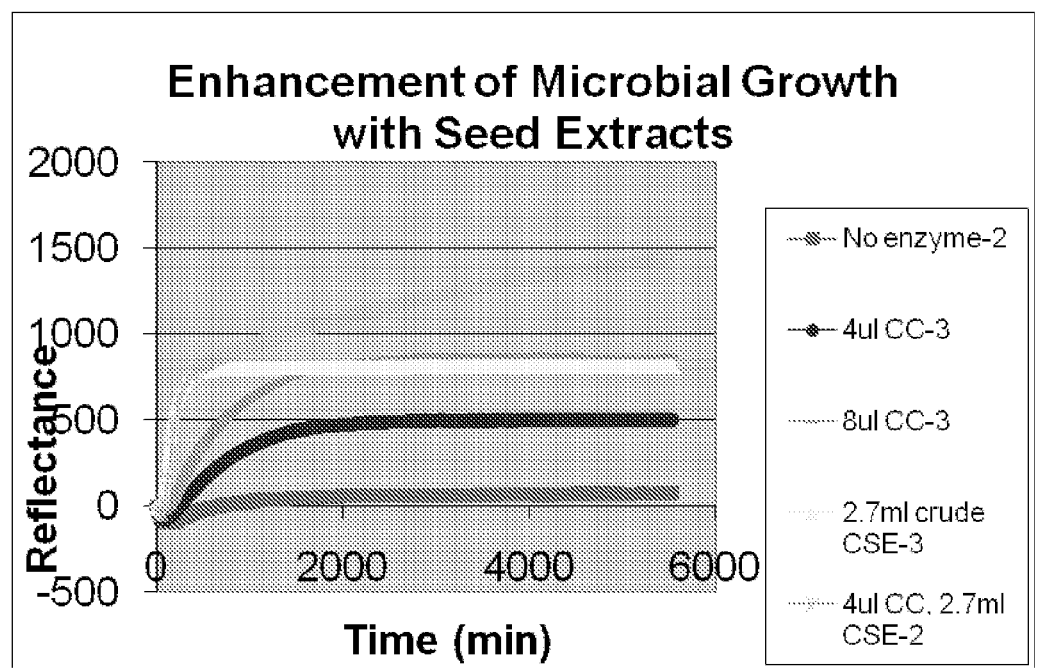
FIG. 11 is a graph showing color change (measured as/reflectance) correlated with yeast growth over time where no enzyme was added, varying concentrations of the commercial mixture were added, and seed extract (CSE) alone or with the microbial cellulase mixture were added as measure by BacT/Alert.

The above experiment provides a useful measurement of the activity and is simple method to detect the synergistic activity but as it only measures glucose. We repeated the experiment and analyzed total free sugars using HPLC as described in methods. The results in FIG. 10A show that the amount of glucose detected by HPLC agreed well with that obtained by the GLOX method. In addition to glucose, cellobiose was also observed to accumulate (FIG. 10B) and that in the presence of CSE the amount of cellobiose was equivalent to that when twice as much Celluclast was used. No other sugars were detected. The above results indicate the synergistic activity but do not rule out the possibility that this approach may produce factors that would inhibit the growth of microbes to produce ethanol. We therefore also performed a microbial growth assay as described earlier to ensure that this approach would not interfere with simultaneous saccharification and fermentation or subsequent fermentation. The results in FIG. 11 show reflectance as measured by the BacT/Alert system an indication of yeast growth that correlates with the release of fermentable sugars. Treatments include; no enzyme, varying concentrations of the commercial enzyme mixture, seed extract (CSE) alone or, seed extract with the commercial mixture. This demonstrates the same trend observed in by the previous assays showing a synergistic rate when CSE is combined with cellulase. Furthermore as this method monitors growth over time it appears that the CSE allows for a longer period of growth than that observed with cellulase alone.

Effect of Desalting Seed Extract on Free Sugar Release

Figure 12:
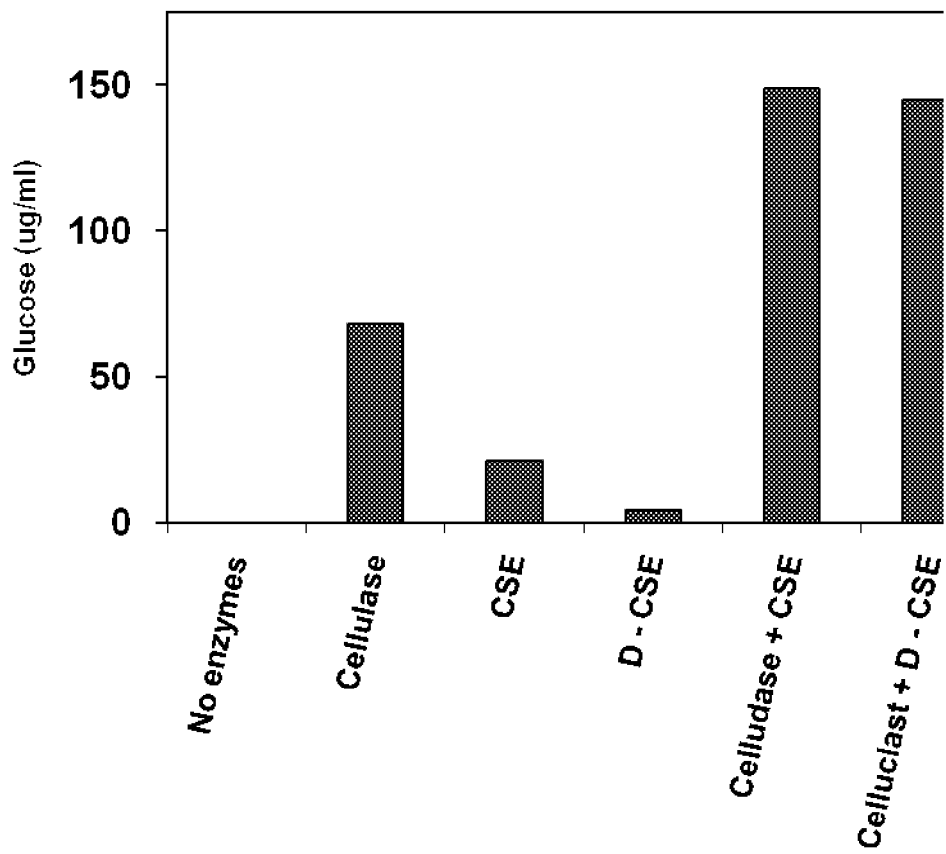
FIG. 12 is a graph showing glucose release using crude seed extracts with (D-CSE) or without (CSE) desalting in combination with commercial cellulase (CC). The results show there is little difference in the enhancement of the commercial enzymes with or without desalting the seed extract.

Since each production step such as desalting adds to overall costs and time, we also tested glucose release without desalting to examine if desalting had a major effect or could be eliminated. Effect of desalting seed extract on free sugar production are shown in FIG. 12. The effect of desalting seed extract was tested after a 24 hour incubation as described in Materials and methods. The effect of combination of Celluclast and CSE was greater than a simple additive effect, whether or not the extract was desalted. The results in FIG. 12 indicate that the desalted seed extract (D-CSE) and the crude seed extract (CSE) significantly increased the release of free sugars when combined with commercial enzymes (CC). This suggests that either CSE or desalted CSE could be used in the reactions without problems of introducing inhibitors of cellulase activity. This also reflects the synergistic factor is at least 10,000 Daltons.

Example 6

Figure 13:
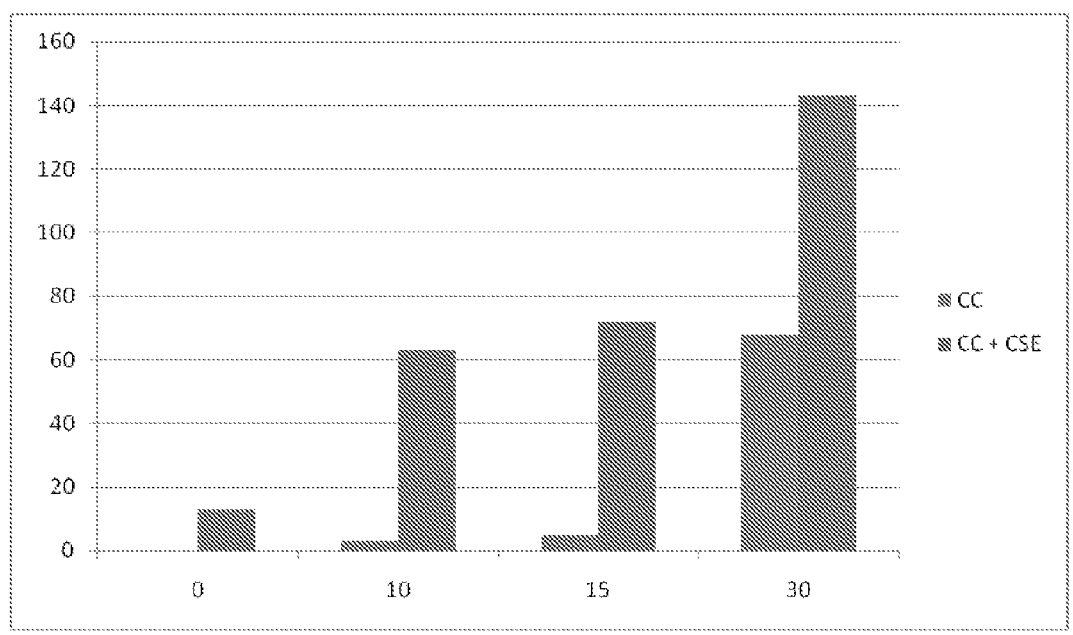
FIG. 13 shows the effect of varying the concentration of commercial cellulase on glucose production, with CC showing increasing amounts of commercial cellulase concentrations without any plant tissue composition added and CC+CSE showing glucose production with increasing amounts of commercial cellulase concentrations with plant tissue composition added. The greatest amount of synergistic activity is seen at low concentrations of cellulase and synergistic activity appears to lessen as the concentration of the cellulase increases.

We examined the effect of varying concentrations of the commercial cellulase (Celluclast) on enhancement of glucose release using a fixed amount of CSE. FIG. 13 shows that the addition of commercial enzyme preparation (CC) at increasing concentrations without any addition of seed extract compared to the same concentrations of commercial enzyme with seed extract added (CC+CSE). The results in FIG. 13 show an increase that is ~20-fold at low cellulase concentrations and drops to ~2-fold when higher amounts of cellulase are used.

Example 7

Figure 14:
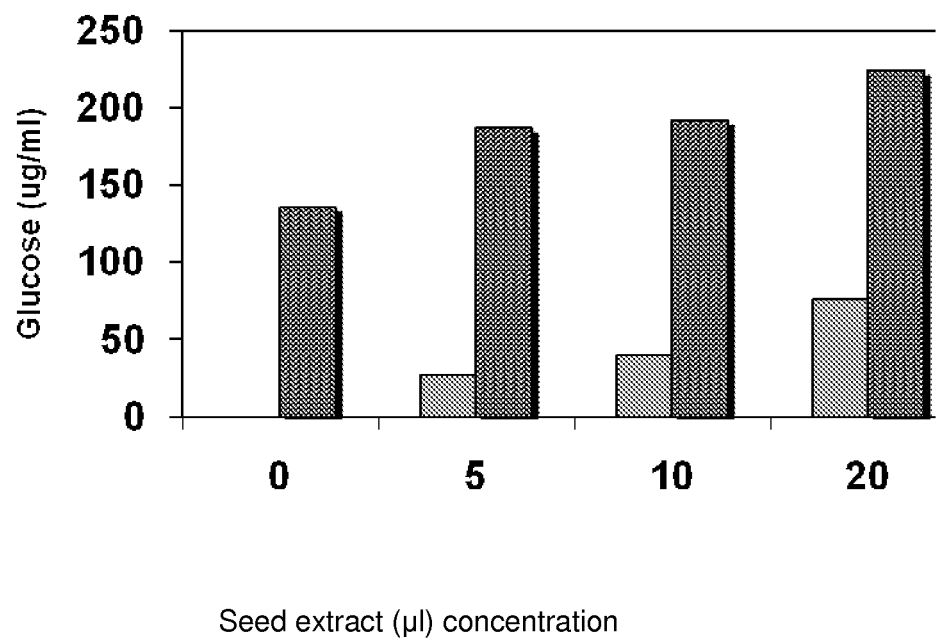
FIG. 14 is a graph showing glucose produced using varying seed extract concentrations (μl extract denoted on x axis) combined with a fixed amount of commercial cellulase.

In a reciprocal experiment, the same procedures were used as above, and instead effect of varying seed extract concentrations was assessed after 24 hours using a fixed amount of Celluclast. Amounts of 0 µl, 5 µl, 10 µl or 20 µl seed extract was added to 30 nl CC or buffer, and results summarized in FIG. 14.

Example 8

Figure 15A:
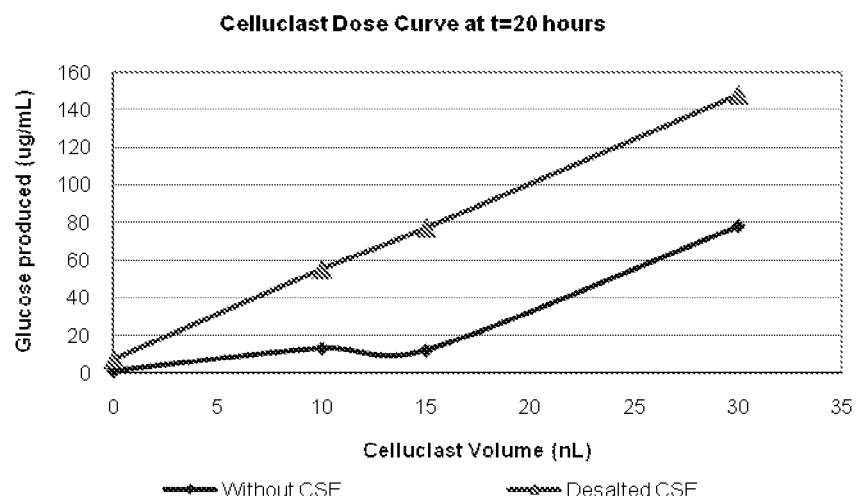
FIG. 15 is a graph showing varying concentrations of three different commercial enzyme mixtures (15A,B,C) with or without CSE.
Figure 15B:
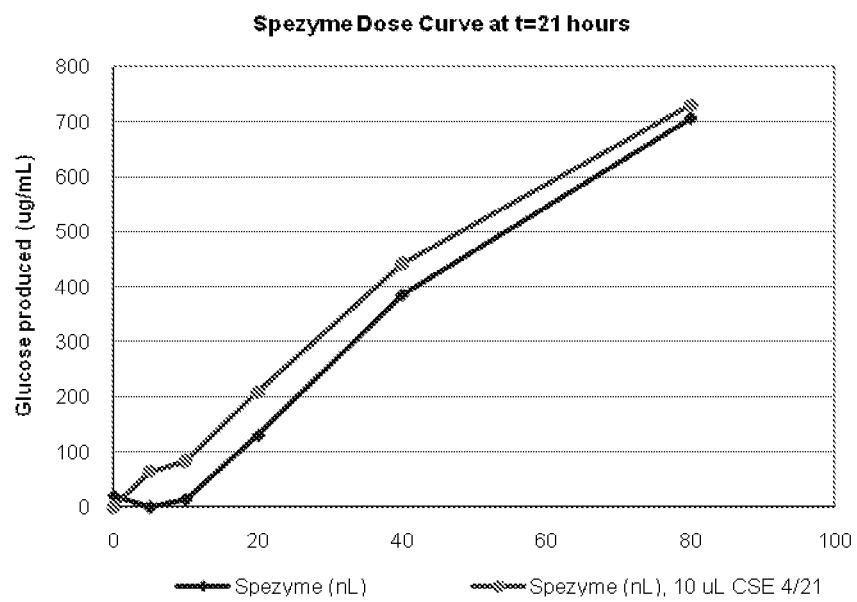
Figure 15C:
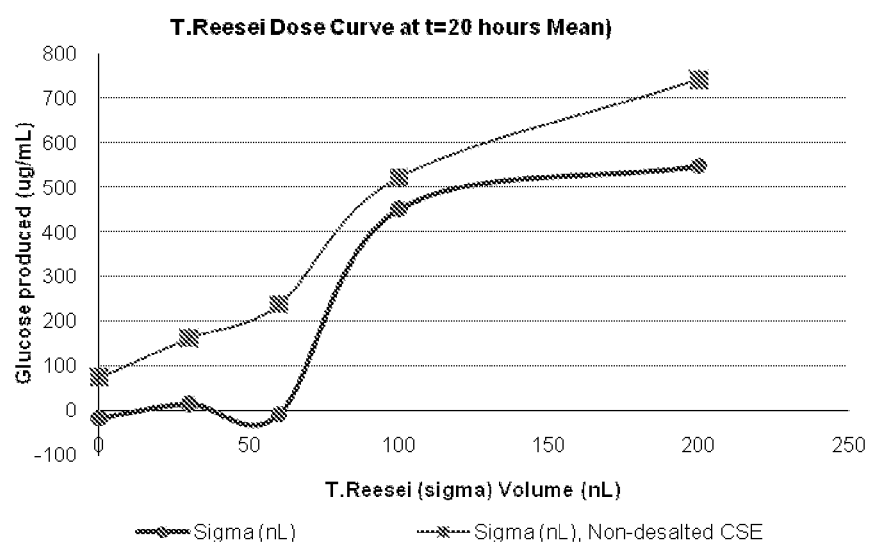

To determine if this potentiation of enzyme activity by seed extracts three different microbially-produced cellulase preparations. The results summarized in FIGS. 15A, 15B and 15C show that the synergistic effect was seen with three different preparations of cellulases. Thus, this effect is a generalized effect that is not dependent on the source of cellulase, and should be applicable to any industrial setting as a way to lower enzyme requirement through improved enzyme activity.

Example 9

Figure 16:
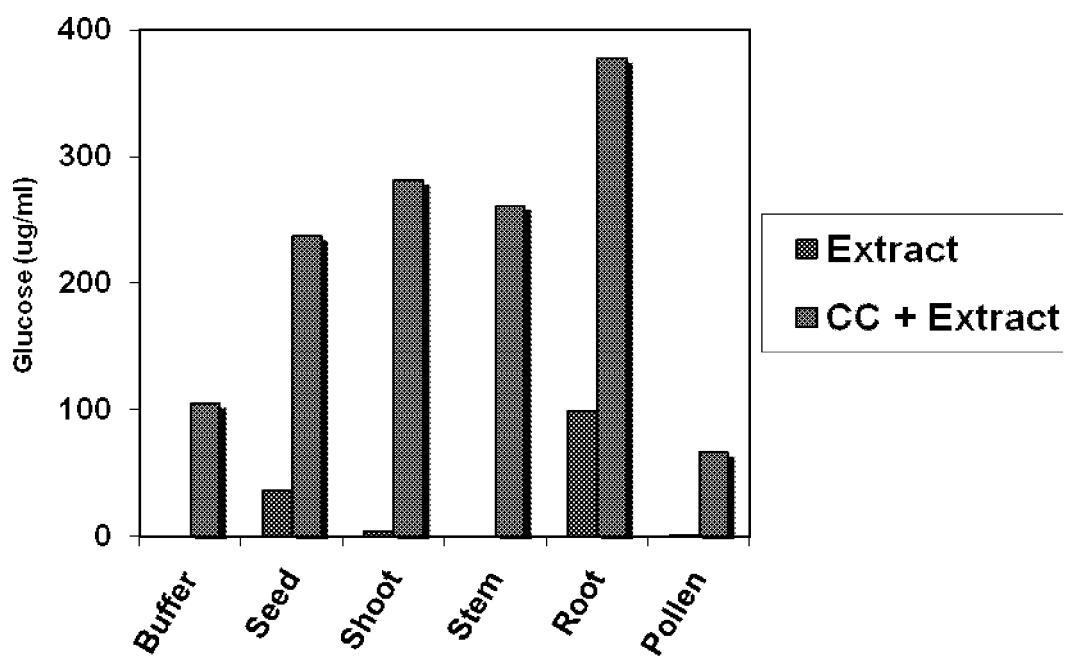
FIG. 16 is a graph showing extracts from various maize tissues combined with cellulose and a commercial cellulase mixture. Glucose production is measure as an indicator of synergistic activity as measured by GLOX. CC alone showed negligible glucose production.

Results were also examined using seed, shoot, stem, root and pollen as a source of the extract. 10 µl of seed extract is ~3 mg/ml. Other extracts were added to achieve the same protein loading. Extracts used=75 µl roots; 30 µl shoots and stems; pollen 0.75 µl; seed 10 µl; used 30 nl of commercial enzyme mix (CC). FIG. 16 summarizes the results.

Example 10

Figure 17:
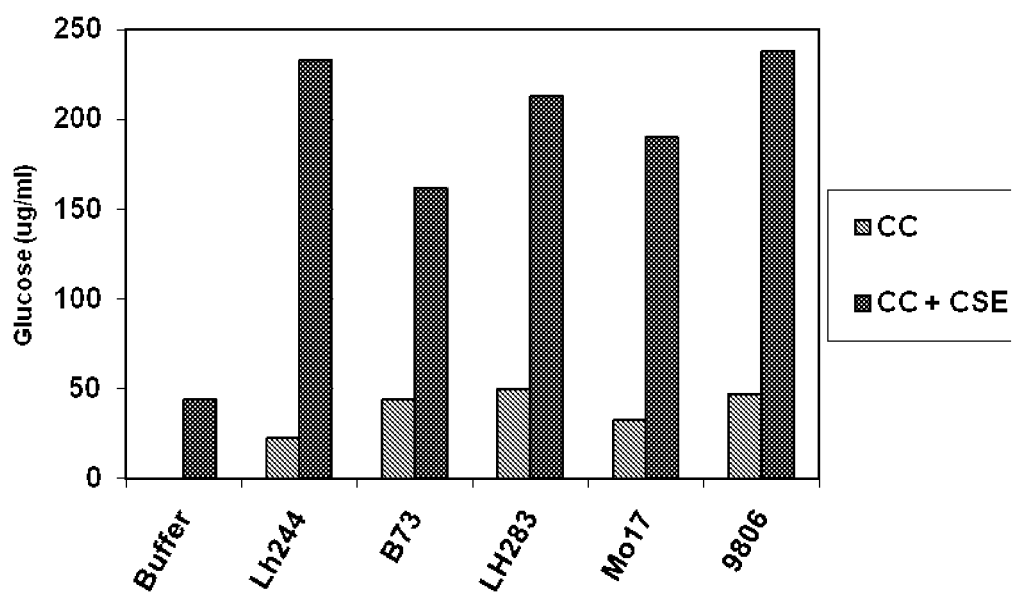
FIG. 17 is a graph showing amount of glucose produced when cellulose was combined with cellulase mixture using various types of maize germplasm seed extracts. CC alone showed negligible glucose production.

A variety of genetic backgrounds are available for the generation of transgenic plants, and these were tested. Seven different germplasm extracts of corn were assessed for synergistic activity by incubation with Celluclast and Sigmacel followed by sampling at 20 hours and measurement of free glucose levels. Those tested included LH244 (described at U.S. Pat. No. 6,252,148); LH283, (see U.S. Pat. No. 5,773, 683); widely available inbred lines B73 (See, e.g., Wei et al. (2009) PloS Genetics 5 (11):e1000715) and Mo17 (See. e.g., Davis et al. Maize Genetics Conference Abstracts, p. 76 (2002)). Equal concentrations of germplasm extract were incubated with varying concentrations of Celluclast for 20 hours and glucose levels were measured. 15 ul commercial enzyme mix (CC) was used as a control. See FIG. 17. All the germplasm tested showed higher free glucose potentiation levels than either Celluclast or the extract alone.

Example 11

Figure 18:
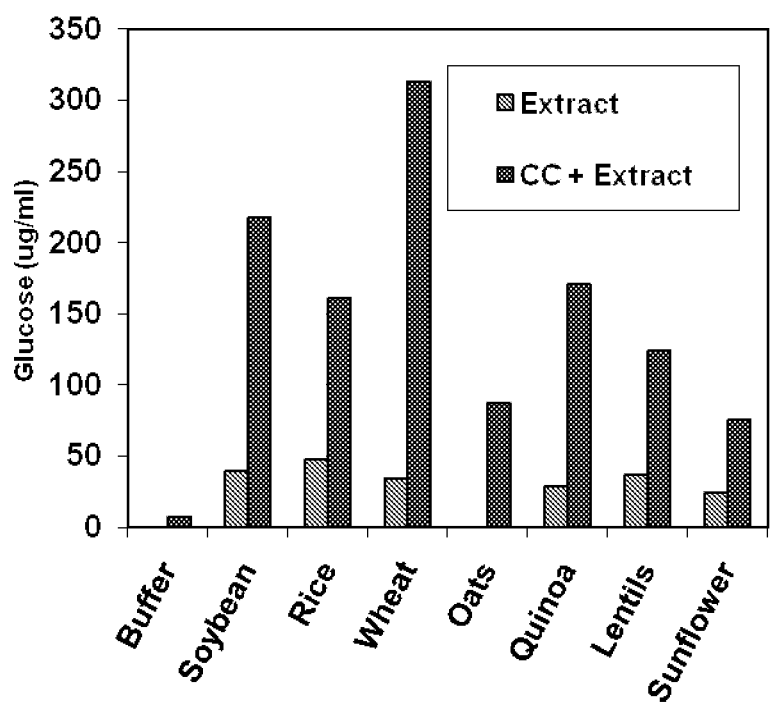
FIG. 18 is a graph showing the amount of glucose produced when cellulose was combined with or without a cellulase mixture and various types of plant seed extracts. CC alone showed negligible glucose production.

Other plants were examined for similar synergistic potential. 10 ul of seed extracts from oats, lentils, rice, soybean, sunflower, wheat and quinoa were prepared and incubated with increasing concentrations of the commercial mix (Celluclast) of endo, exo glucanase and β-glucosidase, were examined. Free glucose present was measured at 20 hours. Compared to Celluclast™ alone control, all of the seed extracts used showed moderate to substantially higher free glucose production, with quinoa and wheat seed extracts showing the highest levels of potentiation of Celluclast activity. Results are summarized in FIG. 18.

Example 12

Figure 19:
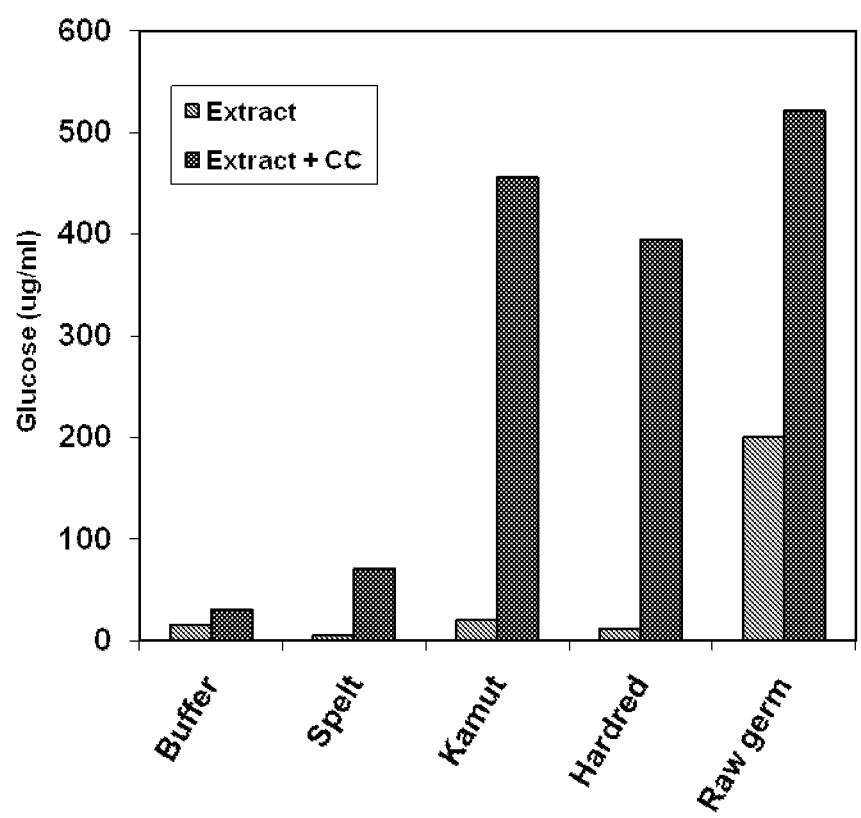
FIG. 19 is a graph showing glucose production when cellulose was combined with a cellulase mixture with and without various wheat tissue sources of wheat extracts.

Since wheat extract showed one of the higher levels of potentiation of free glucose release with Celluclast, this seed was examined further using wheat fractions. Kamut, spelt, raw wheat germ, hard red wheat were tested for glucose production from Sigmacel at varying concentrations of Celluclast at 24 hours. Fractions of wheat: Kamut, wheat germ, spelt, hard red wheat seed and Celluclast alone control were tested at various Celluclast concentrations at 24 hours. All wheat extracts showed synergistic activity with Celluclast, but some quantitative differences were apparent between the lines tested. The most striking difference was that when wheat germ was used there was a high level of glucose produced in the absence of cellulase. This might indicate a higher glucose background in the wheat germ extract but still substantial, synergistic activity. All the remaining fractions showed high synergy with Celluclast with a strong dose-response curve increasing to 700 ug/mL of glucose at 24 hours and 60 uL of Celluclast. FIG. 19 summarizes results.

Example 13

Figure 20:
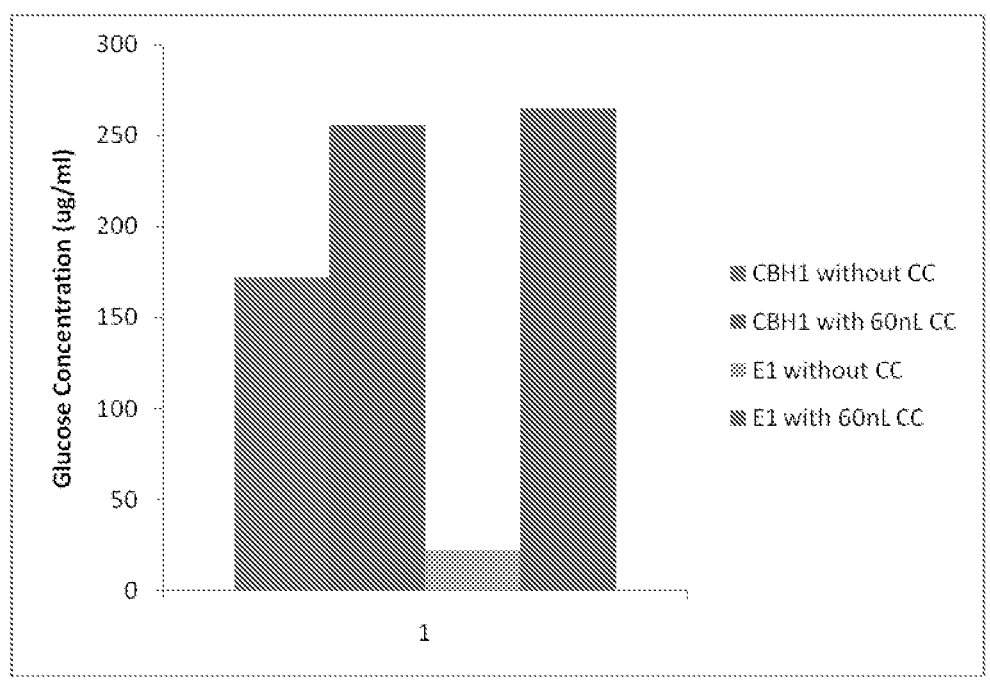
FIG. 20 is a graph showing production of glucose when cellulose is combined with plant tissue composition having heterologous exo-β-1,4-glucanase (CBH1) added without commercial cellulase enzyme mix and with commercial enzyme mix (CC) added; and heterologous endo-β-1,4-glucanase (E1) without commercial enzyme mix added and with commercial enzyme mix added (CC).

Pretreated hardwood treated with cellulase (60 µL) and under these conditions gave negligible glucose. Extracts of transgenic seeds of plants transformed with E1 endocelase as described in Example 2, and transgenic seed of plants transformed with the CBH I exocellulase as described in Example 3 were prepared as described in those examples. The CBH1 and E1 extracts were able to produce glucose from the wood pulp with no commercial cellulase mix added, and when combined with commercial cellulase (Celluclast) as shown in FIG. 20 free sugar production was enhanced further even though there was no significant activity with the commercial cellulase alone.

Example 14

Figure 21:
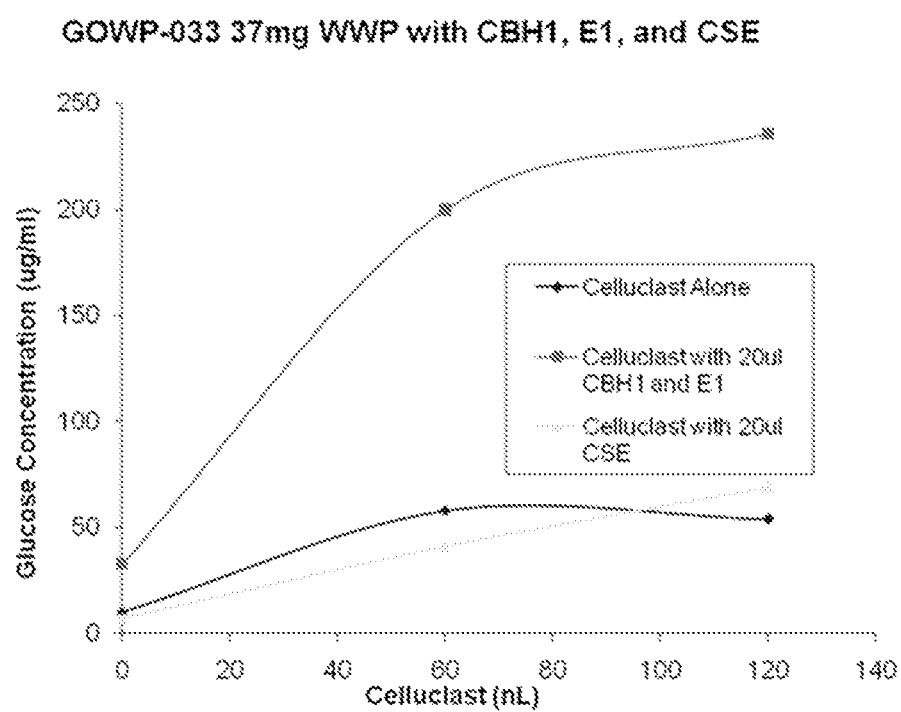
FIG. 21 is a graph showing production of glucose when cellulose is combined with commercial enzyme mix alone (Celluclast), with commercial enzyme mix and transgenic germ extract expressing CBH1 and E1, and where commercial enzyme mix is combined with control germ extract.

In this modification the experiment was carried out with extracts from maize germ and higher concentrations of cellulose, nearly 20 times more, combined with control germ extract (CSE), extracts with CBH1 and E1, and higher levels of commercial cellulase (Celluclast), nearly 100 times more. Results are shown in FIG. 21. The results show that the CBH1 and E1 extracts can triple the amount of glucose released compared to that of using commercial cellulase alone. Extracts from control germ extracts did not have any added effect with the commercial enzymes as predicted at these higher concentrations of cellulose.

To achieve enhanced cellulose degrading activity with extract from plant, it is anticipated that concentration of non-transgenic extract will be increased or provided in higher volume.

Example 15

Maize germ was used without extraction and as the sole source of cellulose. Free sugars were released from the germ under conditions compatible with the saccharification process and no inhibitory factors were indicated.

Figure 22:
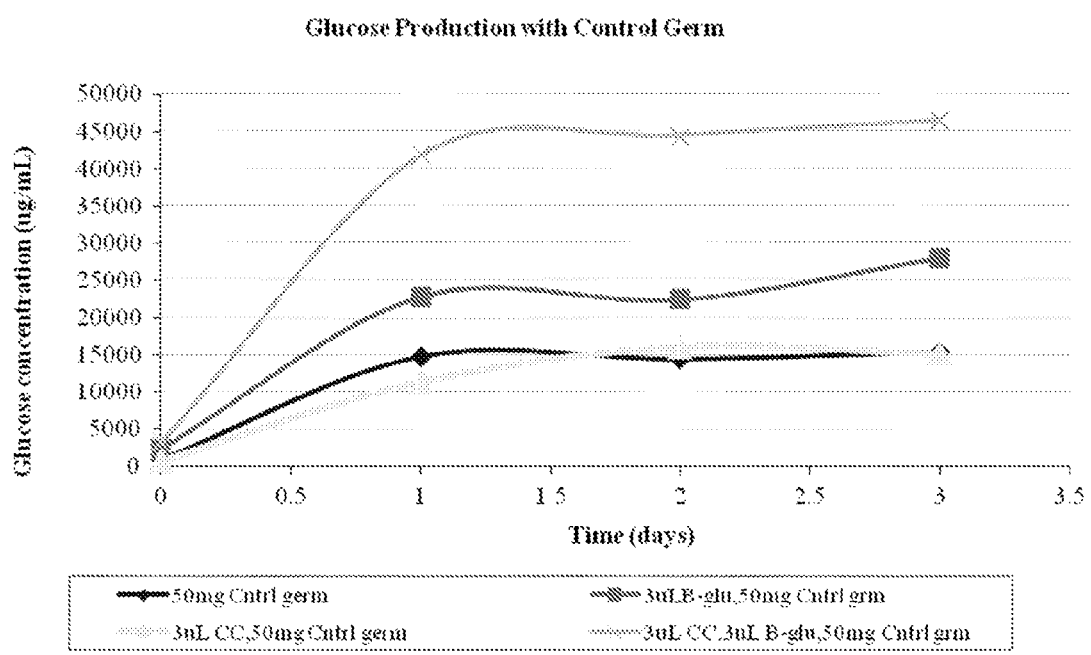
FIG. 22 is a graph showing glucose production when non-transgenic germ tissue is incubated with commercial enzyme mix (CC) and with or without β-glucosidase.

Germ was incubated with and without Celluclast and without any wood products. A typical result is shown in FIG. 22 that indicates that at time 0 there is only a small amount of glucose present but after two days the reaction appears to be nearly complete. The control germ appears to convert some glucose in the absence of Celluclast. It is believed this may be because endogenous β-glucosidase activity that we have seen observed previously in germ is sufficient to convert cellobiose to glucose. Alternatively the glucose may not be derived from cellulose but rather starch in the germ. Maize germ tissue is known to contain starch degrading enzymes and while they could be potentially inactivated in a conventional wet milling process in which high temperatures, well above 100° C. are employed, the enzymes could survive at lower temperatures and in a dry milling operation where there is no extreme heat. In any event, glucose was released from the germ and when Celluclast was added greater amounts were released especially in the presence of β-glucosidase.

The above experiment was repeated with germ expressing cellulase to demonstrate it could lower the amount of commercial enzyme mix used to produce glucose. These results indicate that there is glucose released from the germ even in the absence of any microbial enzymes. This demonstrates that additional glucose credits can be obtained from the germ to offset the cost of the cellulase. Regardless of the mechanism, the above data demonstrate that germ can contribute glucose credits as well as cellulase under conditions used to treat wood products.

Next, we wanted to determine if the transgenic maize germ could provide enough cellulase to release glucose form the germ as well reduce the amount of commercial enzyme mix required for pretreated wood. To account for the additional cellulose from the germ, we calculated 20% of the dry weight of the germ as cellulose and an additional 10% as free sugars based on literature values. Therefore, 30% of the dry weight was used to calculate the percent conversion efficiencies from germ. The composition of the pretreated wood was 62% cellulose and free sugars. The amount of glucose released was determined for the various treatments and the conversion efficiency calculated based on the amount of free sugars and cellulose from germ plus pretreated wood. The results for the various treatments are shown below in Table 3. Several observations can be made from these results. First, there was no appreciable amount of glucose released from the pretreated wood alone but when Celluclast was added glucose accumulated to 7.6 mg for a 21% conversion efficiency (determined by the measuring the final volume of liquid in the reaction and multiplying this by the concentration of glucose). The addition of control germ with wood product adds to the total amount of cellulose (52 mg versus 37 mg) and without the addition of Celluclast, 4.4 mg of glucose was released and with Celluclast this increased to 6 mg. When CBHI or E1 germ was added without Celluclast 7.1 mg and 13.2 mg glucose was released respectively. This is of particular significance for the E1 germ in that the conversion efficiency takes into account the added glucose potential form the germ. The highest amounts of glucose were obtained with a mixture of E1 and CBHI germ. After consideration of the additional cellulose contribution from the germ, this gave the highest overall conversion efficiencies with or without Celluclast (45% and 36%). These results indicate that the cellulase containing germ can contribute to the release of glucose on both the germ itself as well as the pretreated wood.

Thus it is seen that control germ produces glucose. Transgenic germ expressing a cellulase with or without added enzymes produces glucose as well and shows synergy.

TABLE 3

| Treatments All contain β-glucosidase Glucose measured after 6 days | Biomass from wood (mg) | Cellulose from wood (mg) | Biomass from germ (mg) | Cellulose from germ (mg) | Total Cellulose (mg) | Total Glucose produce (mg) | % Conversion |
| --- | --- | --- | --- | --- | --- | --- | --- |
| Buffer Ctrl | 50 | 37 | 0 | 0 | 37 | 0.2 | 0.6 |
| CC | 50 | 37 | 0 | 0 | 37 | 7.6 | 21.0 |
| Ctrl Germ | 50 | 37 | 50 | 15 | 52 | 4.4 | 8.0 |
| CC + Ctrl Germ | 50 | 37 | 50 | 15 | 52 | 6.0 | 12.0 |
| CBHI germ | 50 | 37 | 50 | 15 | 52 | 7.1 | 14.0 |
| E1 germ | 50 | 37 | 50 | 15 | 52 | 13.2 | 25.0 |
| E1 germ + CBHI germ | 50 | 37 | 100 | 30 | 67 | 24.0 | 36.0 |
| E1 germ + CBHI germ + CC | 50 | 37 | 100 | 30 | 67 | 30.0 | 45.0 |

Example 16

In addition to seed extracts and whole germ, tissue such as seed, leaves, stem, roots and plant tissue can be prepared by a grinding process and isolated. Further, whole seed and endosperm tissue is isolated from plants. The tissue composition is treated as described in Example 5 for GLOX with the following treatments: In one treatment, cellulose alone is provided, in another tissue composition alone is combined with cellulose, in another tissue composition and an enzyme is combined with cellulose where the enzyme is an endocellulase or is an endocellulase and exocellulase or is an endocellulase and exocellulase and β-D glucosidase. Measurement of glucose production is expected to occur when plant tissue composition is combined with cellulase and at least one endocellulase, and is expected to be increased compared to the same enzyme combination which does not include plant tissue composition.

What is claimed is:
1. A method of reducing cost of producing glucose from cellulosic biomass, the method comprising,
    (a) providing cellulosic biomass comprising cellulose;
    (b) providing an exogenous cellulose degrading composition at a first amount, said composition comprising a first amount of each of endo-β-1,4-glucanase, exo-β-1,4- glucanase, and β-D glucosidase, said composition capable of converting a first amount of cellulose to a first amount of glucose within 72 hours after contact of said cellulose with said cellulose degrading composition;
(c) providing a plant embryo tissue composition wherein any endogenous enzymes in said plant embryo tissue are capable of converting said first amount of cellulose to a second amount of fermentable sugar within 72 hours after contacting said cellulose with said plant tissue composition;
(d) contacting said plant embryo tissue compositions, said cellulose degrading enzyme composition and said cellulosic biomass;
(e) reducing cost by a process elected from
  (i) providing said cellulosic biomass wherein said cellulosic biomass comprises plant embryo tissue, and not removing or reducing any lignin in said cellulosic biomass prior to contact with said cellulose degrading composition;
  (ii) providing said cellulosic biomass is plant embryo tissue and not adding further cellulosic biomass;
  (iii) excluding from said cellulose degrading composition β-D glucosidase and producing glucose;
  (iv) excluding from said cellulose degrading composition β-D glucosidase and/or one of endo-β-1,4-glucanase or exo-β-1,4-glucanase, and producing at least the same amount of glucose as said first amount of glucose;
  (v) providing said exogenous cellulose degrading composition or at least one of said endo-β-1,4-glucanase, exo-β-1,4-glucanase or β-D glucosidase at a lower amount compared to said first amount and producing at least at least the same amount of glucose as said first amount of glucose;
  (vi) producing glucose within 72 hours after contact of said cellulose with said cellulosic biomass, cellulose degrading composition and said plant tissue composition at a third amount that is greater than the total of said first amount of glucose and said second amount of glucose; and
(f) producing glucose, wherein cost of producing said glucose is reduced.

2. A method of reducing cost of producing glucose from cellulosic biomass, the method comprising,
(a) providing cellulosic biomass comprising cellulose;
(b) providing an exogenous cellulose degrading composition at a first amount, said composition comprising a first amount of each of endo-β-1,4-glucanase, exo-β-1,4-glucanase and β-D glucosidase enzyme, said composition capable of converting a first amount of cellulose to a first amount of glucose within 72 hours after contact of said cellulose with said cellulose degrading enzyme composition;
(c) providing a corn embryo tissue composition wherein any endogenous enzymes in said plant tissue are capable of converting said first amount of cellulose to a second amount of glucose within 72 hours of contacting said cellulose with said corn embryo tissue composition;
(d) maintaining said corn embryo tissue composition at a temperature that does not equal or exceed 120° C. for 15 minutes or longer;
(e) contacting said corn embryo tissue composition with said cellulose degrading enzyme composition and said cellulosic biomass;
(f) reducing cost by a process elected from
  (i) providing said cellulosic biomass wherein said cellulosic biomass comprises corn embryo tissue, and not removing or reducing any lignin in said cellulosic biomass prior to contact with said cellulose degrading enzyme composition;
  (ii) providing said cellulosic biomass is corn embryo tissue and not adding further cellulosic biomass;
  (iii) excluding from said cellulose degrading composition β-D glucosidase and producing glucose;
  (iv) excluding from said cellulose degrading composition β-D glucosidase and/or one of endo-β-1,4-glucanase or exo-β-1,4-glucanase, and producing at least the same amount of glucose as said first amount of glucose;
  (v) providing said exogenous cellulose degrading composition or at least one of said endo-β-1,4-glucanase, exo-β-1,4-glucanase and β-D glucosidase at a lower amount compared to said first amount and producing at least at least the same amount of glucose as said first amount of glucose;
  (vi) producing glucose within 72 hours after contact of said cellulose with said cellulose degrading composition and said plant tissue composition at a third amount that is greater than the total of said first amount of fermentable sugar and said second amount of glucose; and
(g) producing glucose, wherein cost of producing said glucose is reduced.

3. A method of reducing cost of producing glucose from cellulosic biomass, the method comprising,
(a) providing cellulosic biomass comprising cellulose;
(b) providing an exogenous cellulose degrading enzyme composition at a first amount, said composition comprising a first amount of each of endo-β-1,4-glucanase, exo-β-1,4-glucanase and β-D glucosidase, said composition capable of converting a first amount of cellulose to a first amount of glucose within 72 hours after contact of said cellulose with said cellulose degrading enzyme composition;
(c) providing a plant embryo tissue composition wherein any endogenous enzymes in said plant tissue are capable of converting said first amount of cellulose to a second amount of fermentable sugar within 72 hours of contacting said cellulose with said plant tissue composition;
(d) maintaining said plant embryo tissue composition at a temperature that maintains cellulase enhancing activity of said tissue;
(e) contacting said plant embryo tissue composition with said cellulose degrading enzyme composition and said cellulosic biomass;
(f) reducing cost by a process elected from
  (i) providing said cellulosic biomass wherein said cellulosic biomass comprises plant embryo tissue, and not removing or reducing any lignin in said cellulosic biomass prior to contact with said cellulose degrading enzyme composition;
  (ii) providing said cellulosic biomass is plant embryo tissue and not adding further cellulosic biomass;
  (iii) excluding from said cellulose degrading composition β-D glucosidase and producing glucose;
  (iv) excluding from said cellulose degrading composition β-D glucosidase, and/or one of endo-β-1,4-glucanase or exo-β-1,4-glucanase and producing at least the same amount of glucose as said first amount of glucose;
  (v) providing said exogenous cellulose degrading composition or at least one of said endo-β-1,4-glucanase, exo-β-1,4-glucanase and β-D glucosidase at a lower amount compared to said first amount and producing at least the same amount of glucose as said first amount of glucose;

(vi) producing glucose within 72 hours after contact of said cellulose with said cellulose degrading composition and said plant tissue composition at a third amount that is greater than the total of said first amount of fermentable sugar and said second amount of glucose;

(g) producing glucose, wherein cost of producing said glucose is reduced.

4. A method of reducing cost of producing glucose from cellulosic biomass, the method comprising, (a) providing cellulosic biomass comprising cellulose;

(b) providing an exogenous cellulose degrading enzyme composition at a first amount, said composition comprising a first amount of at least one exogenous enzyme, said composition capable of converting a first amount of cellulose to a first amount of glucose within 72 hours after contact of said cellulose with said cellulose degrading enzyme composition;

(c) providing a plant embryo tissue composition wherein any endogenous enzymes in said plant tissue are capable of converting said first amount of cellulose to a second amount of fermentable sugar within 72 hours of contacting said cellulose with said plant tissue composition;

(d) contacting said plant embryo tissue composition with said cellulose degrading enzyme composition and said cellulosic biomass;

(e) reducing cost by producing glucose within 72 hours after contact of said cellulose with said cellulose degrading composition and said plant tissue composition at a third amount that is greater than the total of said first amount of fermentable sugar and said second amount of glucose; and (f) producing glucose, wherein cost of producing said glucose is reduced.

5. The method of claim 4, wherein said plant embryo tissue composition is maintained at a temperature that does not equal or exceed 120° C. for 15 minutes or longer.

6. The method of claim 1, wherein said plant embryo tissue composition is maintained at a temperature that does not equal or exceed 120° C. for 15 minutes or longer.

7. The method of claim 6, wherein said cellulose degrading enzyme composition comprises endo-β-1,4-glucanase and excludes exo-β-1,4-glucanase and β-D glucosidase.

8. The method of claim 6, wherein said cellulose degrading enzyme composition comprises endo-β-1,4-glucanase and exo-β-1,4-glucanase and excludes β-D glucosidase.

9. The method of claim 6, wherein at least one of said endo-β-1,4-glucanase, exo-β-1,4-glucanase or β-D glucosidase is reduced by at least 25% compared to said first amount of said endo-β-1,4-glucanase, exo-β-1,4-glucanase or β-D glucosidase and producing at least said first amount of glucose.

10. The method of claim 6, wherein said at least one of said endo-β-1,4-glucanase, exo-β-1,4-glucanase or β-D glucosidase is reduced by at least 50% compared to said first amount of said endo-β-1,4-glucanase, exo-β-1,4-glucanase or β-D glucosidase and producing at least said first amount of glucose.

11. The method of claim 6, wherein said amount of glucose produced is at least two times more than said first amount of glucose.

12. The method of claim 6, wherein said amount of glucose produced is at least 25% higher than said first amount of glucose.

13. The method of claim 6, wherein said amount of glucose produced is at least 50% higher than said first amount of glucose.

14. The method of claim 6, wherein said plant embryo tissue composition is corn embryo tissue composition.

15. The method of claim 6, wherein said plant embryo tissue composition comprises a heterologous protein selected from the group consisting of endo-β-1,4-glucanase, exo-β-1,4-glucanase and β-D glucosidase.

16. The method of claim 6, wherein said plant embryo tissue composition comprises heterologous endo-β-1,4-glucanase.

17. The method of claim 16, wherein exo-β-1,4-glucanase and β-D glucosidase are excluded from said cellulose degrading enzyme composition.

18. The method of claim 15, wherein said exogenous cellulase comprises said heterologous protein produced by said plant embryo tissue composition and does not comprise additional exogenous cellulase.

19. The method of claim 6, wherein said cellulosic biomass is plant embryo tissue and no further cellulosic biomass is provided and not removing or reducing any lignin in said plant embryo tissue composition prior to contacting said plant embryo tissue composition with said cellulosic biomass.

20. The method of claim 16, wherein said exogenous cellulase comprises said heterologous protein produced by said plant embryo tissue composition and does not comprise additional exogenous cellulase.

21. The method of claim 6, wherein said plant embryo tissue composition is selected from the group consisting of flour, whole embryo, embryo tissue, and extract.

22. The method of claim 6, wherein said plant embryo tissue composition is maintained at a temperature at or below 100° C.

* * * * *